US008852689B2

(12) United States Patent
Srinivas et al.

(10) Patent No.: US 8,852,689 B2
(45) Date of Patent: Oct. 7, 2014

(54) SURFACES HAVING PARTICLES AND RELATED METHODS

(75) Inventors: Arjun Daniel Srinivas, Philadelphia, PA (US); Calvin Peng, Chicago, IL (US); Alexander Chow Mittal, Philadelphia, PA (US); Priyanka Agarwal, Mumbai (IN)

(73) Assignee: Innova Dynamics, Inc., San Francisco, CA (US)

( * ) Notice: Subject to any disclaimer, the term of this patent is extended or adjusted under 35 U.S.C. 154(b) by 1263 days.

(21) Appl. No.: 12/601,869

(22) PCT Filed: May 29, 2008

(86) PCT No.: PCT/US2008/065083
§ 371 (c)(1),
(2), (4) Date: May 28, 2010

(87) PCT Pub. No.: WO2008/150867
PCT Pub. Date: Dec. 11, 2008

(65) Prior Publication Data
US 2010/0230344 A1 Sep. 16, 2010

Related U.S. Application Data

(60) Provisional application No. 60/932,025, filed on May 29, 2007, provisional application No. 61/126,589, filed on May 6, 2008.

(51) Int. Cl.
| | |
|---|---|
| B05D 3/10 | (2006.01) |
| B29C 59/02 | (2006.01) |
| C08J 7/04 | (2006.01) |
| G01N 33/48 | (2006.01) |
| A01N 25/34 | (2006.01) |
| C08J 7/02 | (2006.01) |
| A01N 59/16 | (2006.01) |
| B05D 7/02 | (2006.01) |
| B05D 3/00 | (2006.01) |

(52) U.S. Cl.
CPC .............. *G01N 33/48* (2013.01); *B05D 3/002* (2013.01); *B29C 59/022* (2013.01); *C08J 7/047* (2013.01); *A01N 25/34* (2013.01); *B05D 3/10* (2013.01); *B05D 2401/32* (2013.01); *B29C 2059/023* (2013.01); *B29C 2059/028* (2013.01); *C08J 7/02* (2013.01); *A01N 59/16* (2013.01); *B05D 7/02* (2013.01); *B05D 2601/28* (2013.01)
USPC ............ 427/307; 427/191; 427/322; 427/336

(58) Field of Classification Search
CPC .......... B05D 3/002; B05D 3/10; B05D 3/101; C08J 7/02
USPC .............. 210/285; 252/182.11; 427/180, 314, 427/374.1, 420, 336, 340, 322; 977/742, 977/842
See application file for complete search history.

(56) References Cited

U.S. PATENT DOCUMENTS

| | | | |
|---|---|---|---|
| 3,849,284 A | 11/1974 | Kossmann | |
| 4,604,427 A | 8/1986 | Roberts et al. | |

(Continued)

FOREIGN PATENT DOCUMENTS

| | | |
|---|---|---|
| JP | 2007-39392 | 2/2007 |
| JP | 2009-526132 A | 7/2009 |

(Continued)

OTHER PUBLICATIONS

Riederer, Florian, Supplementary Search Report, Sep. 19, 2011, 8 pgs., European Patent Office, Netherlands.

(Continued)

*Primary Examiner* — Alexander Weddle
(74) *Attorney, Agent, or Firm* — Foley & Lardner LLP; Cliff Z. Liu

(57) ABSTRACT

Particles are embedded in a substrate by applying to at least a portion of the substrate a fluid and a population of particles, such that the substrate is softened to at least a degree that particles are at least partially embedded in the softened portion of the substrate. The softened portion of the substrate is hardened so as to securely embed the particles in the substrate.

16 Claims, 22 Drawing Sheets

(56) References Cited

U.S. PATENT DOCUMENTS

| | | | |
|---|---|---|---|
| 5,071,221 A | 12/1991 | Fujitani et al. | |
| 5,474,814 A * | 12/1995 | Komatsu et al. | 427/549 |
| 5,492,769 A * | 2/1996 | Pryor et al. | 428/552 |
| 5,879,740 A * | 3/1999 | Miyazaki | 427/163.4 |
| 6,156,550 A | 12/2000 | Glad | |
| 6,187,448 B1 | 2/2001 | Hanoka | |
| 6,248,342 B1 | 6/2001 | Trogolo et al. | |
| 6,383,397 B1 | 5/2002 | Kojima et al. | |
| 7,642,463 B2 | 1/2010 | Guiheen et al. | |
| 7,960,027 B2 | 6/2011 | Guiheen et al. | |
| 8,018,568 B2 | 9/2011 | Allemand et al. | |
| 8,049,333 B2 | 11/2011 | Alden et al. | |
| 8,094,247 B2 | 1/2012 | Allemand et al. | |
| 8,138,568 B2 | 3/2012 | Yoon et al. | |
| 8,174,667 B2 | 5/2012 | Allemand et al. | |
| 2002/0115747 A1 * | 8/2002 | Feldheim et al. | 523/201 |
| 2002/0119251 A1 | 8/2002 | Chen et al. | |
| 2002/0175408 A1 * | 11/2002 | Majumdar et al. | 257/734 |
| 2003/0129415 A1 | 7/2003 | Rasmussen et al. | |
| 2003/0157354 A1 | 8/2003 | Vanveghel et al. | |
| 2003/0203207 A1 | 10/2003 | Pessey et al. | |
| 2004/0166166 A1 | 8/2004 | Matsunami et al. | |
| 2004/0169151 A1 * | 9/2004 | Yagi et al. | 250/492.2 |
| 2006/0111008 A1 | 5/2006 | Arthur et al. | |
| 2006/0194037 A1 | 8/2006 | Fink et al. | |
| 2006/0257638 A1 | 11/2006 | Glatkowski et al. | |
| 2007/0065651 A1 | 3/2007 | Glatkowski et al. | |
| 2007/0093181 A1 | 4/2007 | Lugg et al. | |
| 2007/0104605 A1 | 5/2007 | Hampden-Smith et al. | |
| 2007/0196650 A1 | 8/2007 | Yamamoto et al. | |
| 2007/0264481 A1 | 11/2007 | Desimone et al. | |
| 2007/0298253 A1 | 12/2007 | Hata et al. | |
| 2008/0143906 A1 | 6/2008 | Allemand et al. | |
| 2008/0152870 A1 | 6/2008 | Takada et al. | |
| 2008/0193634 A1 | 8/2008 | Yaniv et al. | |
| 2008/0259262 A1 | 10/2008 | Jones et al. | |
| 2008/0276987 A1 | 11/2008 | Flood | |
| 2009/0165844 A1 | 7/2009 | Dutta | |
| 2009/0188697 A1 | 7/2009 | Guiheen et al. | |
| 2009/0229652 A1 | 9/2009 | Mapel | |
| 2010/0012190 A1 | 1/2010 | Goto | |
| 2010/0230344 A1 | 9/2010 | Srinivas et al. | |
| 2011/0139253 A1 | 6/2011 | Wachi et al. | |
| 2011/0217544 A1 | 9/2011 | Young et al. | |
| 2011/0281070 A1 | 11/2011 | Mittal et al. | |
| 2012/0098419 A1 | 4/2012 | Chiba et al. | |
| 2012/0132930 A1 | 5/2012 | Young et al. | |
| 2013/0000952 A1 | 1/2013 | Srinivas | |

FOREIGN PATENT DOCUMENTS

| | | |
|---|---|---|
| WO | WO 2005/061598 A1 | 7/2005 |
| WO | 2005089480 A2 | 9/2005 |
| WO | WO2005/089480 | 9/2005 |
| WO | WO 2007/095058 A2 | 8/2007 |
| WO | WO2008/150867 | 12/2008 |
| WO | WO2010/022353 | 2/2010 |
| WO | WO2010/030374 | 3/2010 |
| WO | WO2010/150619 | 12/2010 |
| WO | WO2011/106730 | 9/2011 |
| WO | WO2012/021460 | 2/2012 |

OTHER PUBLICATIONS

Australian Patent Appln. No. 2008260162, Examination Report (Feb. 6, 2012).

Chinese Patent Appln. No. 200880100186.0, Notification of $2^{nd}$ Office Action (Apr. 28, 2012).

Hu et al., "Scalable coating and properties of transparent, flexible, silver nanowire electrodes." ACS Nano vol. 4:5, 2955-2963 (Apr. 28, 2010).

PCT/US2011/026362, International Search Report and Written Opinion dated Oct. 10, 2011.

PCT/US2009/054655, International Search Report & Written Opinion dated Oct. 19, 2009.

PCT/US2011/046969, International Search Report dated Feb. 20, 2012.

U.S. Appl. No. 13/035,888, filed Feb. 25, 2011, Office Action dated Dec. 22, 2011.

U.S. Appl. No. 13/035,888, filed Feb. 25, 2011, Office Action dated Jul. 19, 2012.

U.S. Appl. No. 13/035,888, filed Feb. 25, 2011, Advisory Action dated Oct. 5, 2012.

$1^{st}$ Office Action in JP2010-510485 dated May 28, 2013.

* cited by examiner

Figure 6 – PRIOR ART
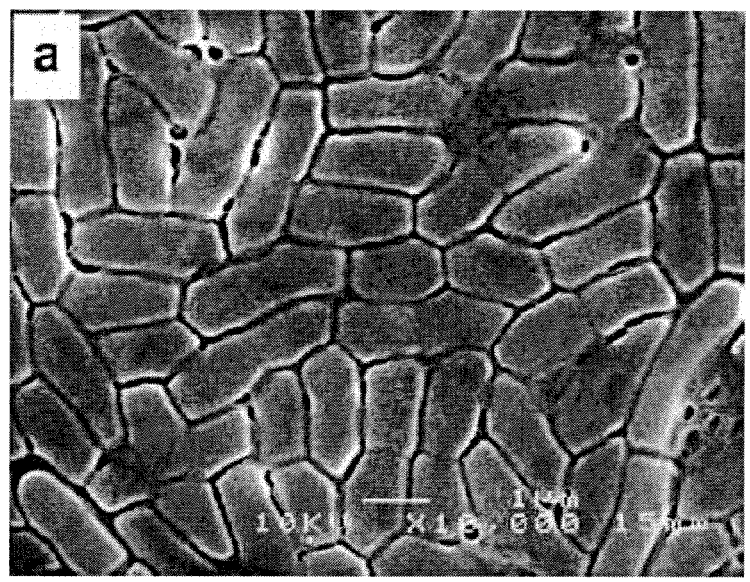
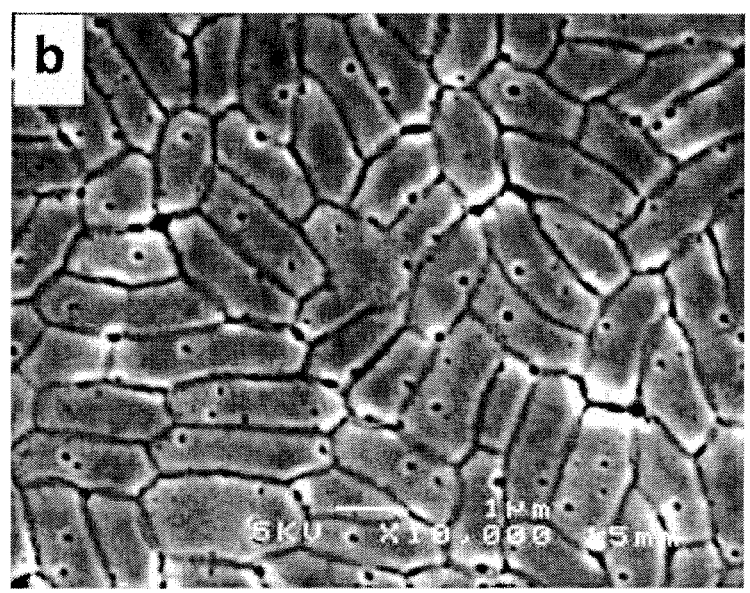

Figure 7
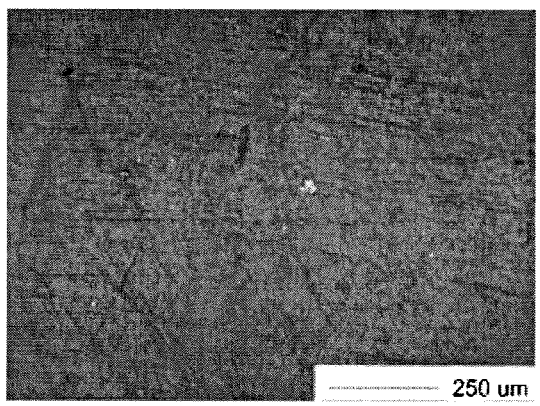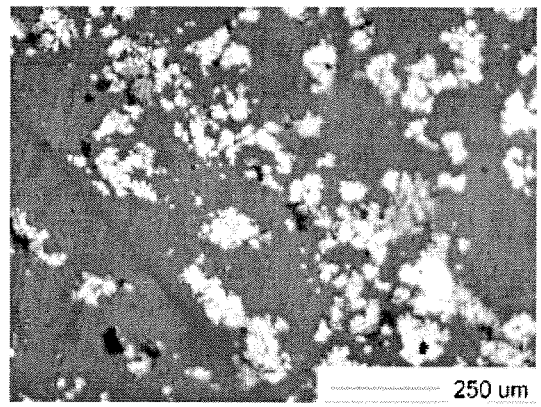

Figure 12
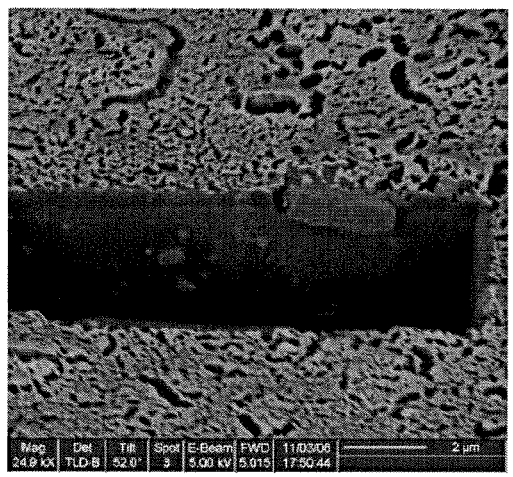 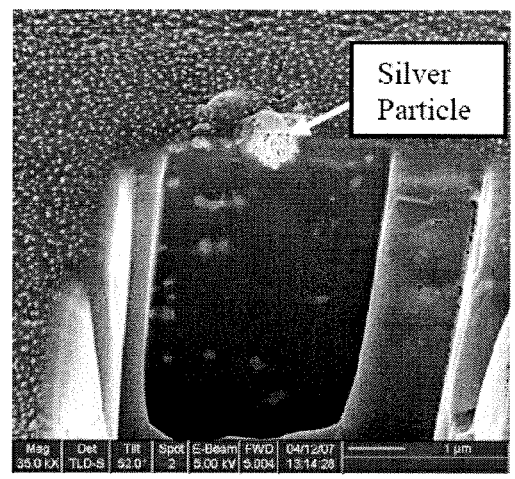

Figure 19
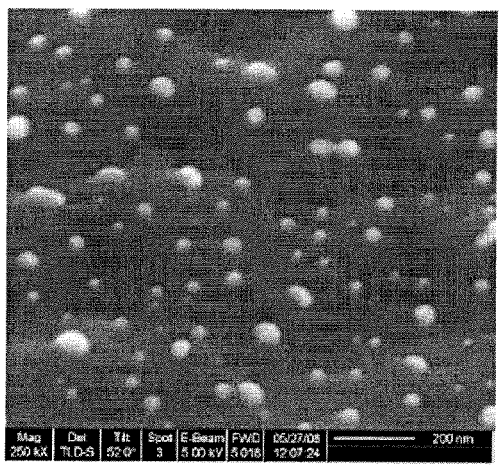 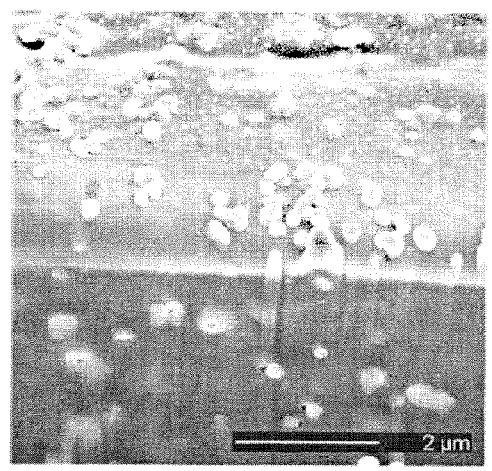

Figure 20
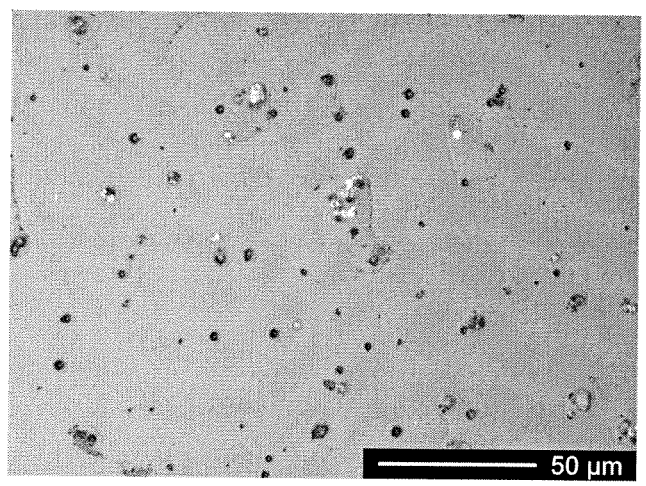
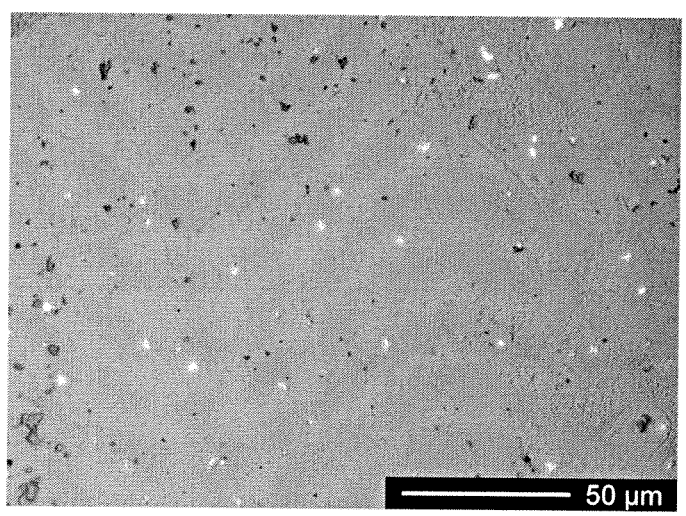

SURFACES HAVING PARTICLES AND RELATED METHODS

CROSS-RERFERENCE TO RELATED APPLICATIONS

This application is the National Stage of International Application No. PCT/US2008/065083, filed May 29, 2008, which claims the benefit of U.S. Provisional Application No. 60/932,025, filed May 29, 2007, and U.S. Provisional Application No. 61/126,589, filed May 6, 2008, the disclosures of which are incorporated herein by reference in their entireties.

FIELD OF THE INVENTION

The present invention relates to the fields of active particles and of polymer-solvent interactions.

BACKGROUND OF THE INVENTION

Functionalizing surfaces by implantation of active, functional particles is an area of interest to a number of fields. By functionalizing surfaces with particles, users may create surfaces that present the useful properties of the particles, such as antimicrobial properties and biosensing.

One area where functionalized surfaces is of particular interest is the reduction of microbial contamination. It is estimated that microbial contamination costs billions of dollars in equipment damage, product contamination, energy losses, and medical infections each year. As one example of the magnitude of this problem, microbial-related damage to buildings and building materials is estimated at several billions of dollars each year.

Microbial contamination also causes significant illness and attendant loss of productivity. Commonly used devices such as phones, automatic teller machines (ATMs), and computer keyboards characteristically present microbial densities many times greater than the microbial densities present on toilet seats and other similar fixtures.

Interest in functional surfaces is not limited to antimicrobial surfaces. As one example, surfaces having the ability to bind to specific biological molecules are also of interest.

Plastics also typically contain a variety of additives—such as plasticizers and lubricants—to help achieve certain desired properties. These additives also, however, provide the carbon needed to sustain the growth and proliferation of microbes. Hence, while plastics typically require one or more additives to achieve a particular characteristic, such additive-laden plastics may also be susceptible to microbial contamination.

At present, substrate-particle composites that include particles of various functionalities are made by two methods. In the common bulk incorporation method of production, particles are non-specifically dispersed throughout the entirety of a substrate. In common coating processes, particles are dispersed within a secondary coating layer that is then disposed atop the main substrate or even atop additional primer or binder layers.

These methods, however, pose certain disadvantages. Bulk incorporation is inefficient in that while the goal of the method is to produce a substrate having particles on the surface, a large number of particles are also dispersed within the substrate. Thus, in bulk incorporation, a large number of particles are effectively buried within the substrate and can not be presented to the environment exterior to the substrate. As a result, a comparatively large number of particles are needed to functionalize the surfaces of a given substrate by way of bulk incorporation. Also, achieving uniform dispersion of particles within the substrate is difficult, but may nevertheless be necessary for uniform surface area coverage of the particles.

Coating processes also present certain inefficiencies. Use of a coating process to make a functionalized surface can involve multiple additional manufacturing steps, including surface pretreatment, priming, and curing. Second, the coating layer must sufficiently adhere or bind to the underlying substrate so as to avoid detachment from the substrate, which is especially challenging for polymer substrates. Proper execution of coating-based techniques may require significant research and development commitments, and may also require additional primer layers or surface treatments. Third, the coating layer must sufficiently entrap particles in order to prevent particles from loosening and escaping under use conditions.

Accordingly, there is a need in the art for composite structures having surface-borne particles that are securely and efficiently attached to the surfaces. The value of such structures would be enhanced if the structures presented such particles on the surface and the structures did not include unnecessary particles within that were not available to presentation to the environment exterior to the structure. There are also parallel needs for fabricating such structures and for other related devices.

SUMMARY OF THE INVENTION

In meeting the described challenges, the present invention first provides methods of embedding particles in a substrate, comprising applying to at least a portion of a substrate a fluid comprising a population of particles having at least one characteristic dimension in the range of from about 0.1 nm to about 1 cm, such that the substrate is softened to at least a degree that a plurality of particles is at least partially embedded in the softened portion of the substrate; and hardening at least a portion of the substrate so as to give rise to at least one particle being securely embedded in the substrate.

The present invention further provides composite materials, the materials comprising a substrate having at least one surface in which a population of particles is at least partially embedded, the population of particles having an average characteristic dimension in the range of from about 0.1 nm to about 1 cm.

Also provided are compositions for functionalizing a substrate, comprising a population of particles disposed in a fluid, the composition being capable of softening a substrate at least to the degree that one or more particles is capable of being embedded at least partially within the softened polymeric substrate.

In addition, the present invention also provides systems for treating a fluid, comprising a structure having at least one surface in which a population of functionalized particles is at least partially embedded, the population of particles having an average characteristic dimension in the range of from about 0.1 nm to about 1 cm; and a supply of fluid.

Further provided is a method of treating targets, comprising contacting one or more targets having one or more components with a surface comprising a population of particles partially embedded in the surface, the population of partially embedded particles comprising an average characteristic dimension in the range of from 0.1 nm to about 1 cm, the contacting being performed so as to give rise to one or more of the partially embedded particles interacting with one or more components of the target.

The present invention also provides methods of embedding particles in polymeric substrates, comprising applying, to a substrate, a population of particles to the substrate under such conditions that one or more of the particles is at least partially embedded in the substrate, the population of particles comprising an average characteristic dimension in the range of from about 0.1 nm to about 1 cm.

Additionally provided are methods of distributing particles across a surface, comprising dispersing a population of particles in a fluid inert to at least one substrate; and disposing the fluid across a surface of the at least on substrate.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 6 illustrates scanning electron micrographs of (a) *E. coli* cells (a) and (b) cells treated with 50 µg/cm$^3$ silver nanoparticles in liquid;

FIG. 7 illustrates optical micrographs of a hot-pressed flat PVC sample having aerosol-delivered silver nanoparticles (right-hand image) and a control sample without silver (left-hand image);

FIG. 12 illustrates SEM micrographs of a trench cut into un-treated PVC (left) and silver-treated PVC (right) exposing a cross-sectional view of an embedded silver particle;

FIG. 19 illustrates SEM micrographs of a PVC surface treated with tetrahydrofuran containing hexadecylamine-capped silver nanoparticles embedded into the surface (left) and a surface (right) exposing a cross-sectional view in the foreground showing the particles embedded deep into the surface;

FIG. 20 illustrates optical micrographs of a polycarbonate surface treated with a 50/50 mix by volume of 2-methyltetrahydrofuran/acetone containing 0.1 wt % Type A zeolite loaded with ionic silver and showing the zeolite crystal particles embedded into the surface (upper image) and a polycarbonate surface (lower image) treated with a 50/50 mix by volume of 2-methyltetrahydrofuran/acetone containing 0.1 wt % zirconium phosphate-based ceramic ion-exchange resin loaded with ionic silver and showing the resin particles embedded into the surface;

DETAILED DESCRIPTION OF ILLUSTRATIVE EMBODIMENTS

Figure 1:
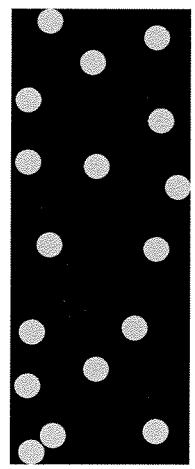
FIG. 1 depicts a schematic cross-sectional view of particles that are bulk-dispersed within a material.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the"

include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In a first aspect, the present invention provides methods of embedding particles in substrates. The claimed methods suitably include applying to at least a portion of a substrate a fluid comprising a population of particles having at least one characteristic dimension in the range of from about 0.1 nm to about 1 cm.

Application of the fluid is suitably performed to give rise to the substrate softening to at least a degree that a plurality of particles is at least partially embedded in the softened portion of the substrate, which softening may be accomplished solely by the fluid in some embodiments.

The embedding of particles is then suitably followed by hardening at least a portion of the substrate. The hardening gives rise to at least one particle being securely embedded in the substrate, as shown in, e.g., FIG. 3 and FIG. 5.

In some embodiments, the population of particles is disposed into the fluid. Disposition may be accomplished by mixing, sonicating, shaking, vibrating, flowing, chemically modifying the particles' surfaces, chemically modifying the fluid, or otherwise motivating or modifying the particles to achieve the desired dispersion. Other methods for achieving particle dispersion in a fluid will be known to those of ordinary skill in the art. The dispersion may be uniform or non-uniform.

The fluid in which the particles reside is suitably a gas or a liquid, and is preferably capable of softening the substrate. The fluid is also suitably inert to the population of particles and does not alter the chemical or other properties of the particles, and the fluid also suitably has little to no effect on the chemical properties of the substrate aside from softening the substrate.

In some embodiments—depending on the needs and constraints of the user—the fluid alters or affects one or more properties of the substrate. For example, the fluid may be chosen for its ability to add functional groups to the substrate or to neutralize functional groups that may be present on the substrate.

Fluids and solvents are, as previously mentioned, suitably chosen on the basis of their ability to soften a particular substrate in a way that is amenable to a user's needs. For example, while a given solvent may be capable of slowly softening a particular substrate, other solvents may be more optimal for a user seeking to quickly soften a substrate for high-speed incorporation of particles into that particular substrate. The effect of the fluid on the substrate may include solely softening the substrate, or may, in some embodiments, also include removal or dissolution of at least a portion of the substrate.

Suitable fluids include—but are not limited to—water, aqueous solutions, organic solvents, inorganic solvents, ionic solutions, solutions comprising salts, and the like. Fluids may be applied under ambient conditions, but may also be applied under heating, cooling, increased or reduced pressure, vibration, sonication, increased or decreased humidity, and the like. The optimal application conditions will be apparent to those of ordinary skill in the art.

Suitable organic solvents include non-polar solvents, polar aprotic solvents, polar protic solvents, and the like. Non-polar solvents include hexane, benzene, toluene, diethyl ether, chloroform, ethyl acetate, and the like—those of ordinary skill in the art will be aware of other non-polar solvents suitable for use in the claimed invention.

Polar aprotic solvents include 1,4-dioxane, tetrahydrofuran, dichloromethane, acetone, acetonitrile, dimethylformamide, dimethyl sulfoxide, and the like. Polar protic solvents include acetic acid, n-butanol, isopropanol, n-propanol, ethanol, methanol, formic acid, and other similar compounds and solutions.

A non-exclusive listing of other, suitable organic solvents includes methyl ethyl keytone, hexafluoroisopropanol, 1-butanol, 2-butanol, 2-butanone, t-butyl alcohol, carbon tetrachloride, chloro benzene, cyclohexane, 1,2-dichloro ethane, diethyl ether, diethylene glycol, diglyme, 1,2-dimethoxyethane, dimethylether, dioxane, ethyl acetate, ethylene glycol, glycerine, heptane, hexamethylphosphoramide, hexamethylphosphorous triamide, methyl t-butyl ether, methylene chloride, N-methyl-2-pyrrolidinone, nitromethane, pentane, petroleum ether, 1-propanol, 2-propanol, pyridine, triethyl amine, o-xylene, m-xylene, p-xylene, trifluoroethanol, diethyl ether, carbon disulfide, mineral oil, isopropylamine, aniline, cycloaliphatic hydrocarbons, tetrahydronaphthalene, tetrachloroethane, tetrafluoropropanol, a fluoro-hydrocarbon, a chloro-hydrocarbon, methyl acetate, methyl formate, a ketone, 2-methyltetrahydrofuran, cyclopentyl methyl ether, methyl n-propyl ketone, a paraffin, an olefin, an alkyne, and other similar compounds or solutions. Alcohols and acids may also be suitable fluids, depending on the substrate and particles being used.

Inorganic solvents suitable for the claimed invention include ammonia, sulfur dioxide, sulfuryl chloride, sulfuryl chloride fluoride, phosphoryl chloride, and phosphorus tribromide. Dinitrogen tetroxide, antimony trichloride, bromine pentafluoride, and hydrogen fluoride are also considered useful.

A variety of ionic solutions are used in the claimed invention. These solutions include choline chloride, urea, malonic acid, phenol, glycerol, 1-alkyl-3-methylimidazolium, 1-alkylpyridinium, N-methyl-N-alkylpyrrolidinium, 1-Butyl-3-methylimidazolium hexafluorophosphate, ammonium, choline, imidazolium, phosphonium, pyrazolium, pyridinium, pyrrolidnium, sulfonium, 1-ethyl-1-methylpiperidinium methyl carbonate, and 4-ethyl-4-methylmorpholinium methyl carbonate.

Other methylimidazolium solutions are considered suitable, including 1-Ethyl-3-methylimidazolium acetate, 1-butyl-3-methylimidazolium tetrafluoroborate, 1-n-butyl-3-methylimidazolium tetrafluoroborate, 1-butyl-3-methylimidazolium hexafluorophosphate, 1-n-butyl-3-methylimidazolium hexafluorophosphate, 1-butyl-3-methylimidazolium 1,1,1-trifluoro-N-[(trifluoromethyl)sulfonyl]methane sulfonamide, 1-butyl-3-methylimidazolium bis(trifluoromethylsulfonyl)imide, 1-butyl-3-methylimidazolium bis[(trifluoromethyl)sulfonyl]amide, and 1-butyl-3-methylimidazolium bis[(trifluoromethyl)sulfonyl]imide.

Halogenated compounds are also suitable. These compounds include N-ethyl-N,N-bis(1-methylethyl)-1-heptanaminium bis[(trifluoromethyl)sulfonyl]imide, ethylheptyl-di-(1-methylethyl)ammonium 1,1,1-trifluoro-N-[(trifluoromethyl)sulfonyl]methanesulfonamide, ethylheptyl-di-(1-methylethyl)ammonium bis(trifluoromethylsulfonyl)imide, ethylheptyl-di-(1-methylethyl)ammonium bis[(trifluoromethyl)sulfonyl]amide.

Imides and amides are also properly included in the claimed invention. A non-exclusive listing of these compounds includes ethylheptyl-di-(1-methylethyl)ammonium bis[(trifluoromethyl)sulfonyl]imide, N,N,N-tributyl-1-octanaminium trifluoromethanesulfonate; tributyloctylammonium triflate, tributyloctylammonium trifluoromethanesulfonate, N,N,N-tributyl-1-hexanaminium bis[(trifluoromethyl)sulfonyl]imide, tributylhexylammonium 1,1,1-trifluoro-N-[(trifluoromethyl)sulfonyl]methanesulfonamide, tributylhexylammonium bis(trifluoromethylsulfonyl)imide, tributylhexylammonium bis[(trifluoromethyl)sulfonyl]amide, tributylhexylammonium bis[(trifluoromethyl)sulfonyl]imide, N,N,N-tributyl-1-heptanaminium bis[(trifluoromethyl)sulfonyl]imide, tributylheptylammonium 1,1,1-trifluoro-N-[(trifluoromethyl)sulfonyl]methanesulfonamide, tributylheptylammonium bis(trifluoromethylsulfonyl)imide; tributylheptylammonium bis[(trifluoromethyl)sulfonyl]amide, tributylheptylammonium bis[(trifluoromethyl)sulfonyl]imide, N,N,N-tributyl-1-octanaminium bis[(trifluoromethyl)sulfonyl]imide, tributyloctylammonium 1,1,1-trifluoro-N-[(trifluoromethyl)sulfonyl]methanesulfonamide, tributyloctylammonium bis(trifluoromethylsulfonyl)imide, tributyloctylammonium bis[(trifluoromethyl)sulfonyl]amide, tributyloctylammonium bis[(trifluoromethyl)sulfonyl]imide, 1-butyl-3-methylimidazolium trifluoroacetate, 1-methyl-1-propylpyrrolidinium 1,1,1-trifluoro-N-[(trifluoromethyl)sulfonyl]methanesulfonamide, 1-methyl-1-propylpyrrolidinium bis(trifluoromethylsulfonyl)imide, 1-methyl-1-propylpyrrolidinium bis[(trifluoromethyl)sulfonyl]amide, 1-methyl-1-propylpyrrolidinium bis[(trifluoromethyl)sulfonyl]imide, 1-butyl-1-methylpyrrolidinium 1,1,1-trifluoro-N-[(trifluoromethyl)sulfonyl]methanesulfonamide, 1-butyl-1-methylpyrrolidinium bis(trifluoromethylsulfonyl)imide, 1-butyl-1-methylpyrrolidinium bis[(trifluoromethyl)sulfonyl]amide, 1-butyl-1-methylpyrrolidinium bis[(trifluoromethyl)sulfonyl]imide, 1-butylpyridinium 1,1,1-trifluoro-N-[(trifluoromethyl)sulfonyl]methanesulfonamide, 1-butylpyridinium bis(trifluoromethylsulfonyl)imide, 1-butylpyridinium bis[(trifluoromethyl)sulfonyl]amide, 1-butylpyridinium bis[(trifluoromethyl)sulfonyl]imide, 1-butyl-3-methylimidazolium bis(perfluoroethylsulfonyl)imide, butyltrimethylammonium bis(trifluoromethylsulfonyl)imide, 1-octyl-3-methylimidazolium 1,1,1-trifluoro-N-[(trifluoromethyl)sulfonyl]methanesulfonamide, 1-octyl-3-methylimidazolium bis(trifluoromethylsulfonyl)imide, 1-octyl-3-methylimidazolium bis[(trifluoromethyl)sulfonyl]amide, 1-octyl-3-methylimidazolium bis[(trifluoromethyl)sulfonyl]imide, 1-ethyl-3-methylimidazolium tetrafluoroborate, N,N,N-trimethyl-1-hexanaminium bis[(trifluoromethyl)sulfonyl]imide; hexyltrimethylammonium 1,1,1-trifluoro-N-[(trifluoromethyl)sulfonyl]methanesulfonamide, hexyltrimethylammonium bis(trifluoromethylsulfonyl)imide, hexyltrimethylammonium bis[(trifluoromethyl)sulfonyl]amide, hexyltrimethylammonium bis[(trifluoromethyl)sulfonyl]imide, N,N,N-trimethyl-1-heptanaminium bis[(trifluoromethyl)sulfonyl]imide, heptyltrimethylammonium 1,1,1-trifluoro-N-[(trifluoromethyl)sulfonyl]methanesulfonamide, heptyltrimethylammonium bis(trifluoromethylsulfonyl)imide, heptyltrimethylammonium bis[(trifluoromethyl)sulfonyl]amide, heptyltrimethylammonium bis[(trifluoromethyl)sulfonyl]imide, N,N,N-trimethyl-1-octanaminium bis[(trifluoromethyl)sulfonyl]imide, trimethyloctylammonium 1,1,1-trifluoro-N-[(trifluoromethyl)sulfonyl]methanesulfonamide, trimethyloctylammonium bis(trifluoromethylsulfonyl)imide, trimethyloctylammonium bis[(trifluoromethyl)sulfonyl]amide, trimethyloctylammonium bis[(trifluoromethyl)sulfonyl]imide, 1-ethyl-3-methylimidazolium ethyl sulfate, and the like.

As will be apparent to those of skill in the art, a variety of solvents are useful, and those of ordinary skill in the art will encounter little difficulty in determining the optimal solvent for use in a given application. Solvents may be chosen based on their compatibility with a particular substrate-particles combination. Alternatively, solvents may be chosen based on their volatility, the classification by governing bodies, or economic constraints of the user.

The fluid may also include salts, surfactants, stabilizers, and other additives that may be useful in conferring a particular property on the fluid. Stabilizers are typically chosen based on their ability to at least partially inhibit inter-particle agglomeration. Other stabilizers may be chosen based on their ability to preserve the functionality of a particle while that particle is being stored or is being incorporated into a substrate according to the claimed methods. Other additives may be used to adjust the fluid's rheological properties, evaporation rate, and other properties.

The fluid may be applied such that it is stationary relative to the substrate. In these embodiments, the fluid is disposed atop the substrate for a period of time. In other embodiments, at least one of the substrate and fluid moves relative to the another—as examples, the fluid may be sprayed on to the substrate, or the substrate may be conveyed through a falling curtain of fluid or conveyed through a pool or bath of fluid. Fluid can also be sprayed, spin cast, dipped, painted on, brushed on, immersed, and the like.

Figure 4:
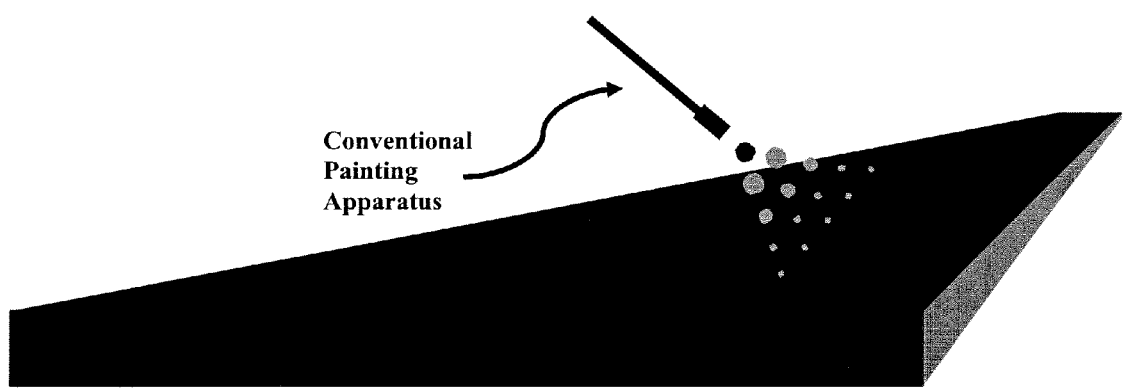
FIG. 4 depicts a schematic view of applying an active material to a substrate according to the claimed invention, using a conventional spray applicator method.

An exemplary view of the claimed methods is shown in FIG. 4, which figure depicts the application of fluid-borne particles to a substrate via a standard painting or coating apparatus. Because the fluid-borne particles may be applied by various means, little to no adaptation of existing application equipment is necessary to perform the claimed methods. The partial embedding of the particles is shown schematically in FIG. 5. The optimal method of applying the fluid to the substrate will be dictated by the needs of the user and will be apparent to those of ordinary skill in the art. In some embodiments, essentially all the particles present in a given finished article are present on the surface of the article, as distinction from the bulk-incorporation articles described elsewhere herein.

Application may be effected by spraying, painting, spin casting, dripping, dipping, dripping, painting, brushing, immersing and the like. In some embodiments, a gradient is applied to the fluid, particles, or both. Suitable gradients include magnetic and electric fields. The gradient may be used to apply or disperse the fluid, particles, or both, to the substrate. In some embodiments, the gradient is used to manipulate one or more particles so as to more deeply embed or drive the one or more particles into the substrate. In other embodiments, the gradient is used to remove or de-embed particles from the substrate.

An applied gradient be constant or variable as dictated by the user's needs. Gradients may be applied before the substrate is softened, while the substrate is softened, or even after the substrate is softened. The strength and orientation of a suitable gradient will be apparent to those of ordinary skill in the art.

The population of particles is suitably essentially uniformly dispersed within the fluid, although non-homogeneous dispersions of particles are within the scope of the present invention. Particles may also be agglomerated, depending on the needs of the user.

The methods also suitably include heating the substrate to at least partially soften at least a portion of the substrate, heating the fluid, heating one or more particles, or any combination thereof. Depending on the particles and substrate involved, application of heat may enhance the embedding of the particles into the substrate.

Particles suitable for the present methods are described in additional detail elsewhere herein, and suitably include one or more functional agents. Functional agents include antimicrobial agents, biocidal agents, insulators, conductors, semiconductors, catalysts, fluorescent agents, flavor agents, catalysts, ligands, receptors, antibodies, nucleic acids, antigens, labels or tags which may be radioactive or magnetic, lubricants, fragrances, and the like. As an example, a particle may include silver or silver ions, which are known to have antimicrobial properties. Other functionalized particles are described elsewhere herein in additional detail.

The particle population applied to the substrate may include two or more particles of different sizes, of different compositions, or even particles of different sizes and different compositions. For example, a user may require a surface that has biocidal properties and possesses a pleasing fragrance. In such a case, the user may utilize biocidal silver particles of one size and fragrant particles of another size.

The particle population may be mono- or polydisperse, depending on the needs of the user and the user's access to particulate materials. The needs of the user will also dictate the composition and distribution of particles used in a given application. In some cases, the monodispersity of the particles embedded in the substrate may be of little to no importance. In other cases, such as where the functionality of the particle-substrate composition depends at least in part on on particle size, monodispersity may have increased importance.

One or more particles may be harder than the substrate prior to the substrate's softening. In alternative embodiments, substrate may also be harder than the particles.

Suitable substrates include polymers, rubbers, woods, and the like. The claimed methods are generally applicable to any material that is capable of being reversibly softened.

Suitable substrates are described in additional detail elsewhere herein and include single polymers or multiple polymers. The claimed methods may also be applied to existing coatings disposed on substrates; for example, the claimed methods are applicable to paints, insulators, and other coatings. Polyvinyl chloride (PVC) is considered an especially suitable for the present invention. Application of the claimed invention to a PVC substrate is described in additional detail elsewhere herein. Polypropylene, polycarbonate, and other common plastics used in consumer and industrial applications are also considered especially suitable.

Wood materials suitable for the claimed methods include hardwood, softwood, plywood, particleboard, fiberboard, and the like. The claimed methods are also suitable for polymer-wood composite materials and engineered wood products.

Following softening of the substrate, the substrate may be hardened by exposure to ambient conditions. In some embodiments, the substrate is hardened by cooling the substrate. In other embodiments, the substrate is hardened by evaporating at least a portion of the fluid, applying airflow to the substrate, applying a vacuum to the substrate, and the like. Combinations of methods for hardening a substrate are also suitable. Other methods for hastening the hardening of the substrate will be apparent to those of ordinary skill in the art.

In some embodiments, the methods result in the particles that are securably embedded in the substrate being distributed essentially uniformly across the substrate. In other cases, the partially embedded particles achieve a non-uniform distribution.

The present invention also includes substrates having particles embedded therein according to the claimed methods.

In another aspect, the present invention provides composite materials. These materials include a substrate having at least one surface in which a population of particles is at least partially embedded, with the population of particles having an average characteristic dimension in the range of from about 0.1 nm to about 1 cm.

Particles may also have characteristic dimensions of from about 1 nm to about 500 nm, or from about 10 nm to about 100 nm, or even in the range of from about 20 nm to about 50 nm. As discussed elsewhere herein, particles may be spherical in shape, but spherical shaped-particles are not necessary to the invention and the invention is not limited to such particles. As non-limiting examples, nanowires and nanotubes—which may have diameters of from 1 to 3 nm and lengths in the multiple-micron range—are suitably used in the claimed invention.

Figure 2:
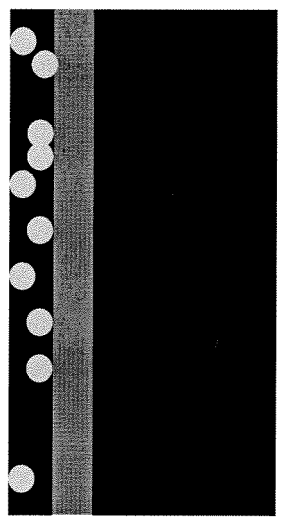
FIG. 2 depicts a cross-sectional schematic view of particles that have been applied to one side of a substrate by a traditional coating method.
Figure 3:
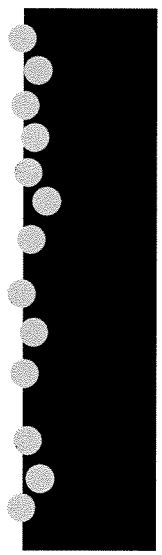
FIG. 3 depicts a cross-sectional schematic view of the claimed materials, depicting a population of particles partially embedded within one side of a substrate material.
Figure 5:
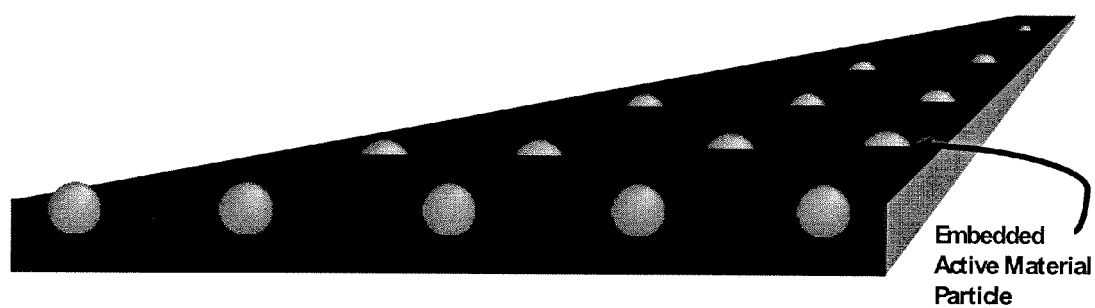
FIG. 5 depicts a schematic view of a several active particles embedded in a substrate according to the present invention.

The particles are suitably partially embedded in the substrate, as shown in cross-section in FIG. 3 and also in FIG. 5. FIG. 3 shows in a cross-sectional view of a structure made according to the claimed invention, particles partially embedded in the surface of the substrate instead of being bulk-incorporated throughout the substrate, as shown in FIG. 1 or being present in a separate coating layer that lies atop a substrate, as shown in FIG. 2. The degree to which a given particle is embedded in the substrate will be a function of a variety of process conditions; those of ordinary skill in the art will appreciate situations where the degree of embedding may be controlled.

Another example of the disclosed compositions is shown in FIG. 19. That figure shows SEM micrographs of a PVC surface treated with tetrahydrofuran containing hexadecylamine-capped silver nanoparticles embedded into the surface (left-hand image) and a surface (right-hand image) exposing a cross-sectional view in the foreground showing the particles embedded deep into the surface.

FIG. 20 illustrates another non-limiting embodiment of the claimed invention. That figure shows optical micrographs of a polycarbonate (PC) surface treated with a 50/50 mix by volume of 2-methyltetrahydrofuran/acetone containing 0.1 wt % Type A zeolite loaded with ionic silver. The upper image in FIG. 20 shows the zeolite crystal particles embedded into the surface. The lower image of FIG. 20 depicts the polycarbonate surface treated with a 50/50 mix by volume of 2-methyltetrahydrofuran/acetone containing 0.1 wt % zirconium phosphate-based ceramic ion-exchange resin loaded with ionic silver, showing the resin particles embedded into the surface.

Figure 21:
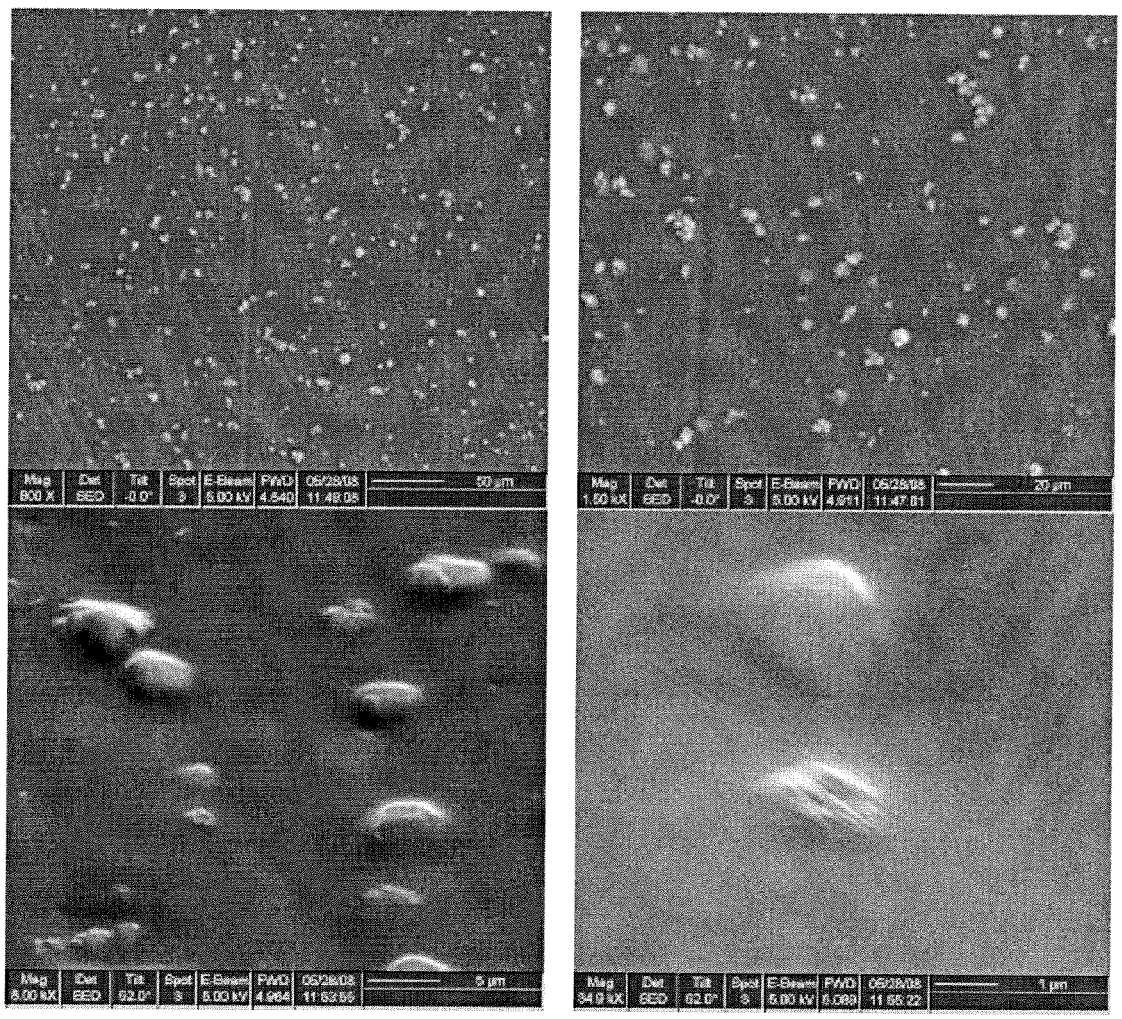
FIG. 21 illustrates SEM micrographs of a polycarbonate surface treated with 2-methyltetrahydrofuran containing 0.1 wt % glass microparticles loaded with ionic silver and showing the particles embedded into the surface.

FIG. 21 shows another exemplary, non-limiting embodiment of the claimed invention. In that figure are shown SEM micrographs of a polycarbonate surface treated with 2-methyltetrahydrofuran containing 0.1 wt % glass microparticles loaded with ionic silver, as is apparent, the particles are securely embedded into the surface.

Figure 22:
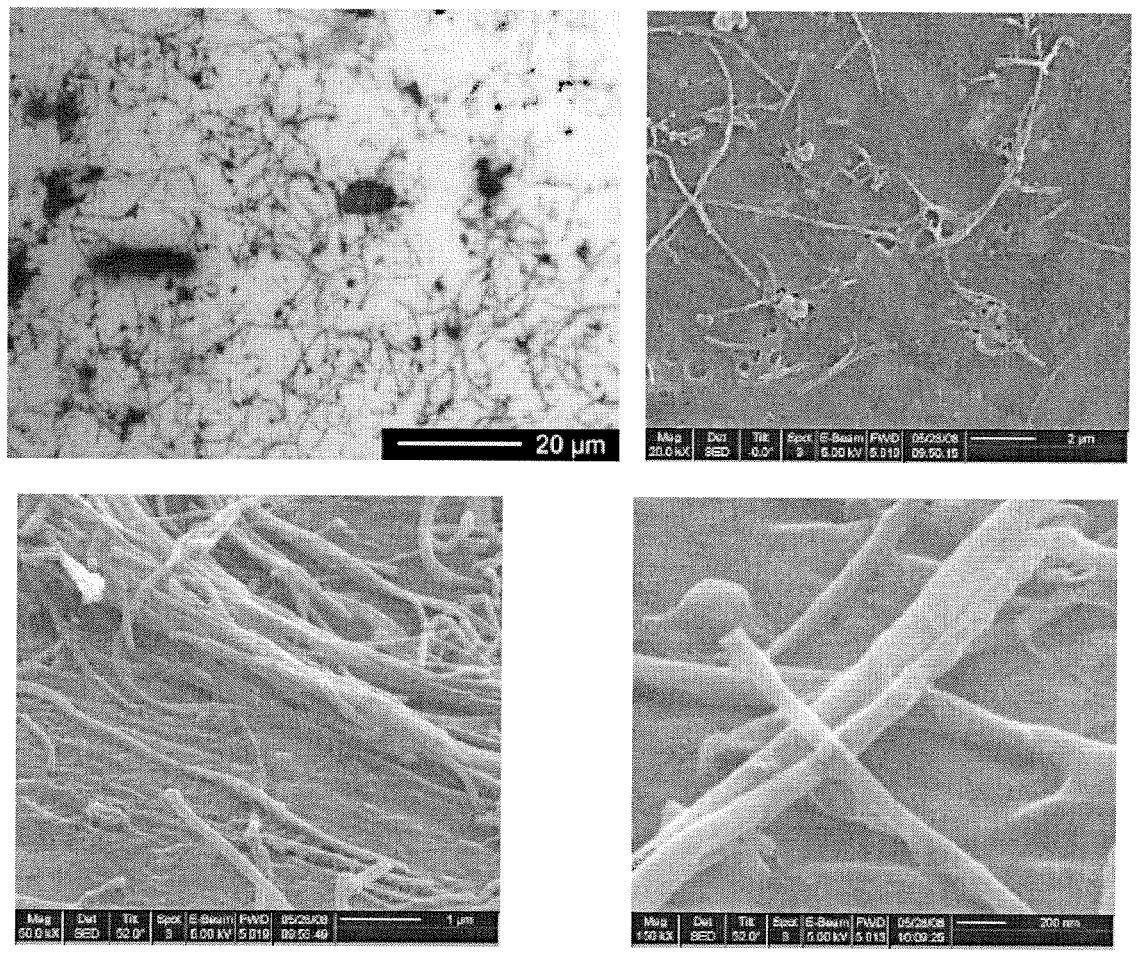
FIG. 22 illustrates (upper left) an optical micrograph of a PVC surface treated with 2-methyltetrahydrofuran containing 0.1 wt % carbon nanofiber, showing nanofibers partially embedded into the surface, and (upper right, lower left, and lower right) SEM micrographs showing the nanofibers partially embedded into the surface.

FIG. 22 illustrates another, alternative embodiment of the claimed invention, which embodiment demonstrates the applicability of the claimed invention to nanofibers. In that figure are shown an optical micrograph (upper left image) of a PVC surface treated with 2-methyltetrahydrofuran containing 0.1 wt % carbon nanofibers, and (upper right, lower left, and lower right) SEM micrographs showing nanofibers partially embedded into the PVC surface.

Suitable substrates include woods, rubbers, polymers, and other materials. Homopolymers, copolymers, random polymers, graft polymers, alternating polymers, block polymers, branch polymers, aborescent polymers, dendritic polymers, and the like are all suitable for use in the claimed composite materials. Polymers classified as thermoplastics, thermosets, or elastomers are all suitable substrates for the claimed materials. Conductive polymers are also considered suitable substrates.

Specifically suitable polymers include polyethylene, polypropylene, polyarylate, polyester, polysulphone, polyamide, polyurethane, polyvinyl, fluoropolymer, polycarbonate, polylactic acid, nitrile, acrylonitrile butadiene styrene, phenoxy, phenylene ether/oxide, a plastisol, an organosol, a plastarch material, a polyacetal, aromatic polyamide, polyamide-imide, polyarylether, polyetherimide, polyarylsulfone, polybutylene, polycarbonate, polyketone, polymethylpentene, polyphenylene, polystyrene, styrene maleic anhydride, polyllyl diglycol carbonate monomer, bismaleimide, polyallyl phthalate, epoxy, melamine, silicone, urea, and the like. Other suitable polymers will be known to those of ordinary skill in the art; cellulosic polymers and other cellulose-based materials are also considered suitable.

Various woods are also suitable for use as substrates in the claimed invention, including hardwood, softwood, plywood, particleboard, fiberboard, chipboard, flakeboard, strandboard, waferboard, and the like. Mahogany, walnut, oak, maple, cherry, rosewod, teak, ash, balsa, basswood, beech, cherry, aspen, birch, buckeye, chestnut, cottonwood, dogwood, elm, hackberry, hickory, holly, locust, magnolia, poplar, alder, redbud, royal paulownia, sassafras, sweetgum, sycamore, tupelo, willow, pine, hemlock, fir, redwood, spruce, cedar, larch, redwood, and other woods are all considered suitable.

The substrate may be solid or porous. In the case of a porous substrate, the composite material, in some embodiments, includes particles disposed on the interior walls of the pores. Such porous composite materials are capable of presenting a comparatively higher surface area—and attendant number of embedded particles—to the surrounding environment than solid substrate.

The optimal choice of particle for a given composite material will depend on the needs of the user. Suitable particles include metals, metal oxides, minerals, ceramics, zeolites, polymers, copolymers, and the like. Silver nanoparticles—having a cross sectional dimension of less than about 100 nm—and silver-based ceramics are considered especially suitable for use in the claimed invention.

Particles suitable for the present invention include one or more functionalizing agents. The material of a particle may itself be functional, or the particle may include one incorporated into or onto a particle, or both. As will be apparent to those of skill in the art, a single particle may present multiple functionalities.

Functionalizing agents suitably include antimicrobial agents, biocidal agents, insulators, conductors, semiconductors, catalysts, UV absorbers, fluorescent agents, flavor agents, catalysts, ligands, receptors, antibodies, antigens, labels, lubricants, and the like. The material from which a particle is made may itself be functional. This is exemplified by silver nanoparticles, which are themselves inherently antimicrobial.

As another non-limiting example, a polymeric particle may include multiple ligands bound to its surface so as to enable specific binding between that particle and a particular target. As another non-limiting example, a silver particle having biocidal properties might also include a fragrant agent so as to impart a pleasing smell to a composite material that has biocidal properties.

As described elsewhere herein, the particles of the composite materials may include particles of the same size or different sizes. The particles may also be of the same or different compositions, and may be mono- or polydisperse. Depending on the user's needs, it may be advantageous to fabricate a composite material that includes several different particles having different functionalized agents so as to provide an article having multiple functionalities.

Both the particles, the substrate, or both, may be porous. Particles according to the present invention may be spherical in shape, but may also be of different shapes. Cylindrical, tubular, cubic, oblong, spheroid, box-shaped, pyramidal, and randomly-shaped particles are all considerer suitable particles shapes. Crystalline shapes—such as tetragons, trigons, hexagons, and the like, are also suitable shapes for particles used in the present invention.

Certain particle types are considered especially suitable for the claimed materials. As discussed, silver and silver-containing particles are considered suitable because of their biocidal properties. Other specific, suitable particles include carbon nanotubes, carbon nanofibers, carbon nanorods, nanowires, buckyballs, nanoshells, liposomes, dendrimers, quantum dots, magnetic nanoparticles, chlorinated rubber particles, glasses, polystyrene microparticles, polymethylmethacrylate particles, melamine microparticles, dextran nanoparticles, melamine-formaldehyde particles, latex particles, divinyl benzene carboxyl particles, divinyl benzene carboxyl sulfate particles, polyvinyltoluene particles, shell-layer particles, copper pyrithiones, radioactive particles, shells, and the like.

Particles may also be chosen based on their inherent properties or other characteristics. These properties include, inter alia, fragrance, flavor, biosensing, ability to bind to biomolecules, color, reflectance, reactivity, catalytic activity, conductive properties, adsorptive properties, insulating properties, semiconducting properties, radioactive properties, antistatic properties, lubricating properties, hydrophobic or hydrophilic properties, and the ability to release one or more agents into the particle's environment.

In some embodiments, essentially all of the substrate's surface is occupied by particles. In other embodiments, 75% or more of the at least one surface is covered by particles, or 50% or more, or 5% or more. In other embodiments, 10%, 1%, or even less of the surface area is covered by particles. The optimal particle coverage will be dictated by the needs of the user—certain composite materials are capable of meeting the user's needs at a surface coverage of only 1% to 10%, as described elsewhere herein.

As described elsewhere herein, two or more of the particles may be agglomerated or otherwise adjacent to one another. Clusters of particles are also suitable in some embodiments.

Separate particles may be separated by distances of from about 0.1 nm to about 1 mm Particles may be separated by uniform or non-uniform distances depending on the needs of the user and the method in which the composite material was formed. In some embodiments, two or more particles are in contact with one another.

Substrates are suitably flat, but may also be cylindrical, polyhedral, spherical, grooved, curved, arced, pitted, hollowed, and the like. The substrate may be in the form of a mesh or filter or other configuration suitable for contacting a flowing fluid while also permitting passage of that fluid.

Substrates are suitably in the range of at least about 0.005 mm in thickness, although thicker and thinner substrates are within the scope of the present invention. Preferably, the substrate thickness is chosen such that softening of the substrate or embedding of the particles does not compromise the integrity of the substrate or impair the functioning of the final, particle-bearing substrate when placed into use.

One or more particles may be selected based on being harder than the substrate. In other embodiments, the substrate is harder than one or more of the particles. In some applications—such as those where the composition may be in physical contact with a moving surface—it may be advantageous to include comparatively hard particles. In other cases, where mechanical removal of particle material is desired, it is preferable to utilize comparatively soft particles.

Substrates are suitably chosen to be inert to the embedded particles. In some cases, the substrate is capable of reaction with one or more particles. As one example, a controlled release material may be made wherein the particle-substrate combination is chosen on the basis that the substrate will degrade the particles—or vice versa—over time so as to effect release of an agent or the material of the particles over time. The optimal combinations of substrates and particles will be apparent to those of skill in the art.

It is envisioned that a composite material made according to the claimed methods is used as a purifier, a sanitizer, a biocide, a detector, a labeler, a filter, a treatment system, or any combination thereof. Several of these applications are discussed in additional detail elsewhere herein.

The present invention also provides compositions for functionalizing a substrate. These compositions include a population of particles disposed in a fluid, where the composition is capable of softening a substrate at least to the degree that one or more particles is capable of being embedded at least partially within the softened polymeric substrate.

Suitable particles and fluids are described elsewhere herein. The composition is useful for functionalizing a variety of substrates, as described elsewhere herein. It is envisioned that the claimed compositions are particularly useful for functionalizing existing substrates, thus enabling modification of legacy systems. As an example, the claimed compositions may be applied to an existing water containment system so as to introduce biocidal particles to the fluid-contacting surfaces of that system, effectively conferring a sanitizing capability on an existing system.

Fluids suitable for the claimed compositions are chosen on the basis of their capability of softening a substrate at least to the degree that one or more particles embeds at least partially within the softened substrate, including when subjected to greater than atmospheric pressure. Fluids may also be suitably selected on the basis of their capability of softening a polymeric substrate at least to the degree that one or more particles embeds at least partially within the softened polymeric substrate when the one or more particles are propelled against the softened polymeric substrate.

The present application also provides systems for treating fluids. These systems suitably include a structure having at least one surface in which a population of functionalized particles is at least partially embedded, the population of particles having an average characteristic dimension in the range of from about 0.1 nm to about 1 mm; and a supply of fluid.

The structures of the systems suitably include substrates and particles, as described elsewhere herein. The structures are configured so as to place a surface comprising one or more partially embedded particles into contact with the fluid in order to afford the particles the opportunity to interact with the fluid. A suitable structure may be a tube, a pipe, a conduit, a container, a sphere, a trough, a mixer, a baffle, a fin, an agitator, a mesh, a screen, a filter, a membrane, a bottle, a barrel, a tank, a channel, and the like. Such structures may be free-standing, as in the case of a pipe. In other cases, the structure is integrated into a device, such as a groove or conduit that is integrated into an analysis or diagnostic device.

Structures may be chosen, constructed, or placed singly or multiply so as to maximize fluid-particle contact. As one example, a series of filter-type structures having the same or different active particles—may be arrayed so as to provide a multi-stage fluid treatment system.

As one example, the structure may be a particle-treated tube through which fluid passes and reacts with the embedded particles. Alternatively, the structure may be a particle-bearing body that is placed in a fluid container and then shaken so as to place the particles into contact with the fluid. Alternatively, the structure may be a particle-bearing bristled body through which fluid is passed.

The systems may also include inlets, outlets, and other fluid passages. A system may also include reservoirs or holding tanks to contain untreated fluids, treated fluids, or both. The structures may include one or more pores if desired; such pores may permit the structure to present increased surface area to fluids with which the structure is contacted. The systems may also include pumps, bellows, and other devices used to actuate fluid flow.

The described systems are suitably used to purify a fluid, decontaminate a fluid, filter a fluid, label, identify, or otherwise react with components within a fluid, and other like applications. Non-limiting examples of these are given elsewhere herein. The systems may be portable or stationary.

The claimed invention also discloses methods for treating targets. These treatment methods include contacting one or more targets having one or more components with a surface comprising a population of particles partially embedded in the surface, where the population of partially embedded particles has an average characteristic dimension in the range of from 0.1 nm to about 1 cm. The contacting is then performed so as to give rise to one or more of the partially embedded particles interacting with one or more components of the target.

Surfaces and particles suitable for use in the claimed treatment methods are described elsewhere. Targets include fluids, solids, gels, biological materials, and the like. For example, a particle-bearing surface may be contacted to a solid—such as a doorknob, a keyboard, or a tabletop. Alternatively, the particle-bearing solid may be contacted to a fluid—such as a water sample or a blood sample.

The contacting is typically accomplished by touching the surface to the target. The target may also be flowed, sprayed, dripped, atomized, overlaid, impressed, nebulized, or otherwise disposed over the surface to achieve contact. Particles may occupy essentially all of the surface area of a surface. In other embodiments, particles may occupy 75% or less of the surface area of the surface, or less than about 50% of the surface area, or less than 10% of the surface area. In some embodiments, surfaces that are 5% or 1% covered by particles are suitable for use in the claimed invention.

Interaction between the particles and the target suitably includes purifying, labeling, disrupting, lysing, binding, chelating, sensing, binding, detecting, and the like. As one illustrative example, a surface bearing a lysing agent is contacted to a cell-containing suspension so as to effect lysing of the cells and the liberation of the cellular contents for further analysis. As another example, a particle-bearing surface where the particles include ligands specific to a particular biological species is contacted to a biological sample that contains that species. The surface then binds that species, immobilizing the species for further analysis.

As one example, a surface bearing particles that are complementary to a specific species may also be used as a filter to remove that species from a given sample. This may be accomplished by, for example, configuring the particle-bearing surface as a filter or other high-surface structure so as to afford the surface the maximal opportunity to contact the sample.

Methods for embedding particles are further disclosed. These methods include applying to a substrate a population of particles to the substrate under such conditions that one or more of the particles is at least partially embedded in the substrate, the population of particles comprising an average characteristic dimension in the range of from about 0.1 nm to about 1 cm; suitable substrates and particles are disclosed elsewhere herein.

Applying the particles is suitably accomplished by propelling, spraying, atomizing, dropping, nebulizing, pouring, dripping, and the like. In one embodiment, the particles are propelled—by, e.g., a sprayer—into the substrate, where they are embedded by impact with the substrate. Particles may also, where suitable, be propelled by an electric field or a magnetic field or other gradient, as described elsewhere herein.

In some embodiments, the particles are disposed in a fluid, as described elsewhere herein. The substrate may also be heated, the particles may be heated, or both.

The present invention also provides methods for distributing particles across a surface. These methods include dispersing a population of particles in a fluid inert to at least one substrate; and disposing the fluid across a surface of the at least one substrate.

The population of particles is suitably evenly dispersed within the fluid. This even disposition may be accomplished by sonicating the population of particles; other methods for even distribution will be apparent to those of ordinary skill in the art. In some embodiments, the fluid, one or more particles, or both, include at least one agent capable of at least partially inhibiting inter-particle agglomeration, as described elsewhere herein. In other embodiments, the dispersion of the particles is at least partly effected by application of a gradient; suitable gradients are described elsewhere herein.

The methods also include removal of at least a portion of the fluid. This is suitably performed so as to leave behind an essentially uniform distribution of particles across the surface. Removal of the fluid may be accomplished by evaporation, application of reduced pressure, and the like.

Additional Non-Limiting Embodiments

Imaging

The process as described in the present application is useful to enhance any polymer containing object with high-contrast agents that can increase the contrast/noise ratio in MRI, X-ray imaging, Computed Tomography (CT), ultrasound, or other imaging tools. The polymer to be treated can be a medical device, a material used during surgery, or any polymer-containing object that may find its way into a body that needs to be imaged.

As one non-limiting example, after surgical intervention in living organisms, it is desirable to confirm that any foreign bodies or objects not intended to be left in the organism are accounted for. In spite of many precautions, foreign materials can be accidentally left in the body, which can compromise patient health. While certain devices, such as stitches and stents, are intended to be left in the body, these devices can be difficult to image. It is thus advantageous that objects involved in a surgical intervention that contain polymeric materials, which tend to have a comparatively low contrast on X-rays, MRIs, or other imaging techniques, be treated with particles that provide higher contrast when viewed with X-rays or MRI or other such technique. Some of these materials and devices include medical devices, medical equipment, medical instruments, stitches, sponges, gauzes, gloves, safety goggles, clamps, and the like.

In typical medical settings, contrast media are used to enhance the visibility of objects. As one example, a radio-opaque substance may be used during an x-ray to enhance the visibility of structures within the body. For MRI imaging, the contrast agents alter the magnetic properties of nearby hydrogen nuclei; such contrast may be positive or negative. Positive contrast media have higher attenuation density than the surrounding tissue—making the contrast look more opaque—while negative contrast media has lower attenuation (i.e., makes the contrast look less opaque). Negative contrast is typically found only as a gas.

The high-contrast agents can be particles as described above but will typically contain elements that have high atomic numbers. Some examples of these particles are: gold particles and nanoparticles, silver particles, copper particles, platinum particles, titanium particles, iodine containing particles or compounds, barium-containing particles or compounds, diatrizoate, metizoate, ioxaglate, iopamidol, iohexyl, ioxilan, iopromide, iodixanol, and the like. Gadolinium-containing particles or compounds can also be used as a component of MRI contrast.

Once the substrate of the material or device to be contrast-enhanced has been identified, a suitable fluid is chosen as a softener for the surface. As described elsewhere herein, there are a number of possible solvents or liquids and combinations thereof that can achieve this purpose, and the optimal combination of materials and fluids will be dictated by the needs of the user. Subsequently, particles that have characteristically high-contrast will be added to the liquid, and will be mixed to achieve some level of uniformity via physical agitation or by adding stabilizers, or by way of certain surface chemistries.

The resulting solution may then be applied to the substrate so as to embed the contrast-enhancing particles in the substrate. The particles will then in turn cause the treated objects to more easily discernible through the imaging and observational techniques referenced above.

Diagnostic Biosensor Applications

The claimed invention also enables diagnostic biosensors for the detection of cancer, genetic disease, and other ailments. For example, to detect certain DNA, RNA, or other nucleic acid sequences, or to detect antigens and other biomolecules, complementary nucleic acid sequences or corresponding antibodies are localized on a polymer substrate such that a positive match between a detector moiety and an antibody leads to a discernible change. For example, metallic nanoparticles such as gold nanoparticles may be embedded in a plastic substrate according to the claimed methods and single-stranded DNA or antibodies may be bound to the nanoparticles through a thiol group or other surface attachment methods. Particles may also be embedded with the biomolecule binding sites already emplaced on the particles prior to embedding.

Following introduction of a solution, e.g., blood, enzyme digested blood, other biofluid, to a plastic surface enhanced in this way, the target DNA, proteins, etc will bind to the nanoparticles. The presence of the target molecules can be detected via a change in voltage, light intensity, mass, or other discernible change, which change may be amplified or otherwise enhanced through the binding of additional particles or markers, e.g. fluorescing molecules, at the location of the binding. Such a device may effect a visible change upon the binding of target compounds, making a separate reader unnecessary for the result of the test. Because the target molecules are bound to the particles embedded in a surface, the bound molecule will likely resist being displaced by moderate rinsing. If stronger methods—such as vigorous rinsing, heating, or the introduction of bond-cleaving agents are used, the target molecules may be displaced, thus permitting re-use of the biosensor.

Electronics Applications

As discussed elsewhere herein, carbon nanotubes, nanowires, and nanoparticles are some of the particle types that may be used for the production of wires, transistors, resistors, capacitors, memristors, and other components of electronic circuits or devices, such as light-emitting diodes (LEDs) through this process, but any of the particles described in this document are applicable.

As one non-limiting example, particles are embedded into the surface of a thin layer of conducting polymer to tune the polymer's electronic properties, e.g., to vary the type or degree of resisting, conducting, and semiconducting. In another example, metallic nanoparticles are embedded in the surface of a polymer to form a conducting path, due to touching or proximity of the particles to one other or due to a heating, reduction-oxidation reaction, or other process to fuse the particles.

As another example, to solve the problems of fluorescent lights burning out or of having a delay before they generate light after electricity is run through them, carbon nanotubes or nanowires or other particles of disproportionate aspect ratio may be embedded into a conducting polymer substrate such one end of the nanotube or nanowire is free of the substrate and capable of emitting electrons upon passage of a current through the conducting polymer. Similarly, nanowires, nanotubes, or particles having disproportionate aspect ratios—again with an unembedded end—may be used as part of a field emission display (FED) or other display technology as a generator of electrons—such as a cathode—to enable the illumination of a pixel or other visible display entity by causing a phosphor or other material to emit light. Wavelengths other than those of visible light may be produced as well.

Embedded particles—again with unembedded ends—may function as part of a probe. This enables massively parallel reading and writing to a storage device or massively parallel AFM or other probe microscopy. Such treated surfaces are also useful as an interface with biological cells or neurons.

In the aforementioned examples involving nanowires, nanotubes, or other particles embedded in a surface but also having an unembedded end, an alternate mechanism could be used to localize the nanowires or carbon nanotubes on the surface. Instead of directly embedding nanowires or carbon nanotubes into the surface such that one end remains unembedded in the surface, catalytic or reactive nanoparticles could be embedded in the surface, which would then catalyze the growth of nanowires or carbon nanotubes at the regions where the nanoparticles had been embedded.

A current passed through the substrate or a field generated around the surface then promotes nanowires or nanotubes having one end extending away from the surface during or after growth. In all of the above examples involving nanowires or carbon nanotubes or other such particles embedded in a conducting polymer surface with an unembedded end, the devices may also function if the substrate is a nonconducting polymer layer coated on top of a conducting substrate, where electrons traverse the nonconducting layer.

Antistatic Applications

Anti-static additives are used in many plastics to inhibit accumulation of electrical charge on the product surface. Because plastics are typically inherently electrically insulating, they have a tendency to accumulate such charge. Antistatic additives reduce and can eliminate the gathering of dust and dirt, lowering the risk of sparks on products such as furniture and flooring, packaging, consumer electronics, and stationary. Without being bound to any single theory operation, it is believe that these additives function by lowering the overall resistivity of the treated article.

Instead of being incorporated into products through bulk incorporation or coating, as is currently done, plastic surfaces can be made antistatic by incorporation of antistatic agents or particles by way of the claimed methods. Various antistatic additives are capable of incorporation into the surface of plastics via the claimed processes; these antistatic particles can be anionic, cationic, non-ionic, or polymeric in nature. The three principal chemistries of these antistatic agents are ethoxylated amine (EA), glycerol monostearate (GMS), and lauric diethanolamide (LDN), each of which is amenable to the disclosed methods and compositions.

RFID (Radio-Frequency Identification) Tags

The process as described in this patent application can be used to create an RFID tag, in a number of different ways. These tags can also be used with frequencies that are not limited to radio frequencies, but can be used with both higher and lower frequencies such as microwaves, infrared, x-rays, and other.

RFID tags normally contain two parts—an integrated circuit for storing and processing information, modulating, and demodulating an RF signal, and an antenna for receiving and transmitting the signal. There are active, passive, and semi-passive RFID tags.

The process described in this patent application can be used to create the antennae that are used to pick up a signal and re-transmit it. The process as described when used in conjunction with conductive particles can be used to create a conducting coil pathway that acts as an antenna. The antennae need not be coil-shaped, and need only be capable of having electrical current induced in the antenna by the incoming frequency signal, or be capable of transmitting an outgoing signal, or both. If the particles embedded in the surface are not touching or do not otherwise form a conducting pathway, the particles can be joined using a number of different methods, including sintering the particles so that they fuse together, or applying a solution containing ions or particles that will deposit as metal onto the embedded particles to fuse particles and form a conductive pathway.

One type of antenna created by the present invention is a magnetic dipole antenna. The reader antenna can be a single coil that is typically forming a series or parallel resonant circuit, or a double loop—transformer—antenna coil.

Magnetic ID Applications

The process described in this patent application can be used to create unique magnetic identifications for the purposes of authentication or tracking. By using the process described in this patent application with magnetic, paramagnetic, diamagnetic, ferromagnetic, antiferromagnetic, ferromagnetic, metamagnetic, superparamagnetic, and other types of particles, unique and non-replicable magnetic signatures are created. Because the particles embedded in such a process are oriented and distributed randomly, each application will have a different configuration.

At present, the traditional magnetic barcode of a credit card can be replicated easily. Replication of a similar barcode made according to the present invention would be more difficult, because the sheer number of particles and the fine distribution of the particles renders the exact magnetic signature statistically less replicable. In other embodiments, by inducing a magnetic field in the environment surrounding the spray environment during spraying and until the surface hardens, a controlled and replicable magnetic pattern may be achieved. Thus, the process described in this application is used to create both extremely random or extremely ordered magnetic patterns on substrates.

Antimicrobial and Toxin-Neutralizing Applications

Polymer surfaces that interface with water, such as bottles, vessels, tanks, pipes, hydration bladders, valves and tubes of hydration packs, filters, valves, and spouts, may be treated by the process described with antimicrobial particles that will protect the surfaces, and also treat the water and deactivate microbial contaminants Examples of such particles include ion-exchanged zeolites, silver-loaded insoluble phosphates, silver-loaded calcium phosphate, silver-ion-modified glass, silver-ion-exchanged potassium titanate fiber, silver-loaded inorganic colloid, silver nano or micro particles, and the same using copper, zinc, or other metallic ions, metallic nanoparticles, ion-loaded glass, ion-exchanged zirconium phosphate-based ceramics and other ceramics, zinc pyrithione particles, copper pyrithione particles, and the like.

The effect of silver nanoparticles is shown in FIG. 6. The left side of that figure depicts a population of *E. coli* bacteria. At the right of FIG. 6 is the same population of bacteria after treatment with liquid-borne silver nanoparticles, which treatment caused the formation of pits—shown as blackened regions—on the bacteria, which increase the bacteria's permeability, which eventually leads to cell lysis.

Aside from embedding antimicrobial particles, other particles may be embedded to impart additional functionality. Particles for neutralizing known toxins and other hazardous chemicals and substances may also be embedded. For example, iron oxide—rust—particles may be embedded to decrease arsenic content of the water interfacing with the surface through adsorption. Iron nanoparticles may also be embedded and used to decrease the concentrations of chlorinated methanes, chlorinated ethenes, chlorinated ethanes, chlorinated benzenes, polychlorinated benzenes, lindane, Cr(VI), Pb(II), Ni(II), Cd(II), perchlorate. Single-wall carbon nanotubes (SWNTs), other sorts of nanotubes, and other carbon structures may be embedded to absorb dioxins and other organic compounds, and can even absorb bacteria and other organisms. Embedded carbon nanotubes could also absorb a variety of other compounds including sodium chloride, sodium sulfate, calcium chloride, magnesium sulfate, sulfuric acid, hydrochloric acid, fructose, sucrose, humic acid, viruses, proteins, and bacteria.

Common objects may also be embedded with antimicrobial-acting particles. A non-exclusive listing of such objects includes keyboards; computer mouse; clear film with pressure sensitive adhesive backing; food containers; water containers and bottles; eating and cooking utensils; shower curtains; water and beverage dispensers; shopping cart handles and shopping carts; hydration packs, bladders, valves, tubing, and bags; water pipes; sewage pipes, gas pipes, footwear, cell phones; video game controllers and buttons; laptop and ultraportable computers, mouse pads and pointing pads; vehicle steering wheels; vehicle plastic surfaces, vehicle buttons, vehicle vents, train and subway supports and handrails; airplane and train tray tables, armrests, windowshades, cutting boards; trash cans; dish drying rack and pan; fish tank tubing; fish tank filters, lobster traps; fish nets and tanks; boat hulls; refrigerator sealing gaskets; refrigerator surfaces; biometric readers such as finger and palm print readers; boat and other water-based propellers; humidifier and dehumidifier tanks and surfaces; shower mat; gym and yoga mat; gym equipment; catheters; intubation tubes; implantable devices and materials; newborn baby holders used at hospitals; premature infant holders; bathroom and shower soap and shampoo dispensers; plastic handles and knobs for doors, cabinets, sinks, showers and similar; ATM keypads; ATM screens and screen protectors; credit cards and other plastic cards; salt, pepper, and similar shakers; athletic helmet straps and interior helmet padding; litter boxes; pet bowls for food and water; pet carriers; subway, train, car, restaurant, or other seats having polymer coverings; table surfaces and counter top surfaces and refinishings; placemats; colanders; tanks; medical tool trays; plastic medical tools, orthodontic devices, table tops, faceplates for consumer electronics; remote controls; tiles, shower surfaces; toilet surfaces; trash bins and lids and handles. Other applications will be apparent to those of ordinary skill in the art.

Catalytics

The process as described above is also applicable to creating catalytic surfaces. The process described above can be with traditional heterogeneous catalysts like vanadium oxide, nickel, alumina, platinum, rhodium, palladium, mesoporous silicates, etc. Similarly, some homogeneous catalysts can be used like: enzymes, abzymes, ribozymes, deoxyribozymes, and the like. Electro-catalysts are also suitable, including, for example, platinum nanoparticles. Organocatalysts are also substances that can suitably be embedded into a surface Application of the claimed invention to catalytics is useful in growth of nanowires, nanorods, or nanotubes, where a gold, silver, or other metallic particle or nanoparticle acts as the growth catalyst. As one non-limiting example, gold nanoparticles may be embedded into substrate and used to grow nanowires, nanorods, or nanotubes, thereby producing a structure having these structures embedded within and projecting outward.

Catalytic converters can also be made using the claimed invention. There are several components of the catalytic converter, the core, the washcoat, and the catalyst itself. The washcoat is a rough surface that increases surface area, and the core is usually a high-surface area support for the catalysts. In standard catalytic converters, platinum and manganese are catalysts that help break down some of the more harmful byproducts of automobile exhaust. The catalyst is normally platinum, but palladium and rhodium are also used. Cerium, iron, manganese, nickel, and copper may also be used. Other metals or catalytic material could also be used. The process described above could be used to embed these catalysts into the core or other parts of the catalytic converter.

Other potential uses would be in catalysis-based chemical production processes like the Haber process, that is used to produce ammonia. This multiple step process uses multiple different types of catalysts. For example, nickel oxide is used during steam reforming, mixtures of iron, chromium, and copper, as well as copper, zinc, and aluminum, are also used during the process as catalysts for different parts of the reaction. In the final stage of the process, magnetite—iron oxide as the catalyst—is used. Other catalysts could be used as well, by using the process described above to embed these catalytic particles into a surface.

This could also be used to create a pipe or container surface that can be used to catalyze a gas or liquid reaction. The process could also be used to create a filter, where as a liquid or gas passes through the filter it contacts the catalytic surface.

Fragrance and Flavor Applications

Products, packaging materials, and films may be enhanced with flavor and fragrance via the process described in this patent application. Compounds capable of providing flavor or fragrance can be incorporated into controlled-release particles may be compatible with the process described in this application. Some applications for odor neturalizing and fragrances include trash bins and toilet seats.

The process as described above can also be used to enhance surfaces with flavors or scents. By using particles like silica shells, absorbent polymer beads, buckyballs, nanotubes, or other encapsulation particles, certain flavors or scents can be captured. Using the process above, one can embed the encapsulated flavors/scents into the surface of things like toys, novelty items, plastic spoons, forks, knives, straws, and other utensils, and dental retainers, pacifiers, animal toys, and the like.

Antimicrobial Testing

The following are exemplary, non-limiting embodiments of the claimed invention as applied to antimicrobial applications. These embodiments do not limit the scope of the claimed invention in any way and are for illustrative purposes.

1. Aerosol Treatment

The conditions of freshly extruded PVC pipe were simulated using a number of methods including via fiber extruder and hot press. Silver powder was then aerosolized onto the molten PVC surface to create a uniform dispersion of particles on the surface. The aerosol generator used was built by linking an air gun to a nanoparticles reservoir and to a thin pipette (which acted as the barrel) via a series of adapters. Bursts of air aerosolized the nanoparticles and pushed them through the pipette and towards the target.

1.1 Fiber Extruder

Using a fiber extruder (DACA Instruments' SpinLine Fiber Extruder), industrial-grade PVC pellets were extruded through a 1 mm diameter aperture. The PVC pellets were heated for 30 minutes to temperatures ranging from 150-185° C. and fibers were extruded at speeds ranging from 1-20 mm/minute. Nanoparticles were aerosolized onto the hot extruded surface.

1.2 Hot Press

Flat industrial-grade PVC samples and freshly extruded PVC samples (fabricated using the fiber extruder, were placed between two steel plates that were heated to temperatures ranging from 150-185° C. and pressed at pressures ranging from 1,000-15,000 lbs. The PVC samples were removed at time periods ranging from 30 seconds to 30 minutes, and were examined Silver microparticles (Powder, 2.0-3.5 µm, 99+%. Sigma-Aldrich, www.sigma-aldrich.com, Cat. No. 327085) were then aerosolized onto the resulting hot and softened PVC surfaces.

2. Solvent Treatment Method 2.1 Substrate Preparation

Flat industrial-grade PVC sheets were used as the substrate for depositing antimicrobial silver treatment. For all tests other than ASTM E2180, these large sheets were cut into 1.2×1.2 cm pieces, using a PVC clamp-cutter (Home Depot, www.homedepot.com). For the purpose of the ASTM E2180 test, PVC sample substrates were cut into 3×3 cm. All PVC substrate samples were washed with soap and water followed by methanol and ethanol.

2.2 Suspension of Silver Nanoparticles

Silver nanoparticles were suspended in tetrahydrofuran (THF), an organic solvent. High molecular weight PVC powder (HMW PVC powder. Fluka <www.sigma-aldrich.com>, Cat. No. 81387) and silver nanopowder (Nanopowder, <100 nm, 99.5% (metals basis) (Sigma-Aldrich www.sigma-aldrich.com, Cat. No. 576832) were added in various weight percentages to THF. The resulting solutions were sonicated to aid the dissolution of the PVC powder and suspension of the silver particles; sonication of PVC in THF prior to addition of silver nanopowder resulted in better suspension formation. The efficacy of PVC powder as a stabilizing agent was investigated by comparing plain silver suspensions to PVC-stabilized silver suspensions. PVC concentrations were varied from 0.0 wt % to 3.0 wt % and silver concentrations were varied from 0.45 wt % to 4.0 wt %.

2.3 Substrate Treatment

The application of silver nanoparticle solutions onto all PVC substrates was accomplished using a spin-coater. The 1.2×1.2 cm samples were spin-coated at 1500 rpm for 33 seconds with 10 drops of silver solution sequentially added immediately after spinning was initiated. The 3×3 cm samples were spin-coated at 3000 rpm for 33 seconds with the equivalent of 10 drops squirted quickly onto the sample immediately after spinning was initiated. The above values for spin-speed, number of drops, and method of applications were chosen after extensive trials for optimizing the embedding of the silver particle as a function of these parameters.

2.4 Characterization Using Raman Spectroscopy

The silver nanoparticles and the surface of silver-treated PVC samples were characterized via Raman spectrometry (Renishaw RM1000 VIS Raman Microspectrometer, Drexel University <www.nano.drexel.edu/Facilities). The silver-treated PVC samples were placed under the optical microscope and were focused at 50× magnification. The optical portion of the spectrometer was then turned off and the green argon-ion laser ($\lambda$=514.5 nm, 1% intensity to prevent sample burn) was focused on the samples. The Raman scattering responses were then measured with 10 passes, approximately 10 seconds each pass, and were analyzed to determine the composition of the targeted area. All scattered intensity data were recorded on a relative scale.

2.5 Characterization Using Optical Microscopy

Optical micrographs of silver-treated PVC surfaces and control samples were obtained and analyzed to characterize the silver treatment. The samples were placed under an optical microscope and focused at 20× magnification, which magnification level was chosen for its wider field of view and superior resolution. ImageJ software (ImageJ; http://rsb.info.nih.gov/ij/) was used to improve image characteristics and measure particle dispersion characteristics, such as average particle size and the area fraction of particle coverage.

2.6 Characterization Using Scanning Electron Microscopy

Nanoscale surface characterization was achieved using the Focused Ion Beam (FIB) SEM10 (FEI Strata DB235, www.fei.com). The silver-treated PVC samples were first sputter-coated with gold palladium for 30 seconds at 30 milliamps and then analyzed using the FIB. In addition to observing the local structure of the silver particles on the sample surface, the FIB was used to cut through a silver particle and into the PVC surface to reveal a cross-sectional view of the embedded particle.

2.7 Durability Testing

Preliminary durability tests were undertaken to assess the effect of continuous water flow over the silver-enhanced PVC surface. Four PVC samples treated with a single silver solution (2 wt % silver and 2.25 wt % PVC powder) were fixed in place and subjected to a continuous stream of water having flow rate of 3.9 gal/min·in². This water flow was produced by altering the flow of water from a common tap using a plastic sheet. Recommended flow rates in commercial PVC pipes used for water transportation were between 0.4 and 8.0 gal/min·in². The sample surfaces were characterized using optical microscopy before the test and after 2.5, 8, 26, and 51 hours. The area fraction of surface coverage of each sample was determined using ImageJ routines.

2.8 Antibacterial Testing

To qualitatively and quantitatively characterize the antibacterial activity of the nanoparticles and of the silver-enhanced samples, a number of tests were used. Kirby-Bauer, Turbidity, Growth Analysis, and ASTM E-2180 tests were conducted. Appropriate controls were used in all tests, and all samples were rinsed with ethanol before use.

2.8.1 Kirby-Bauer

Modified Kirby-Bauer tests were run to qualitatively verify the known antibacterial properties of silver nanoparticles and to qualitatively observe the antibacterial properties of silver-enhanced samples. Sterile, 10 cm Luria-Burtani (LB) plates (1.0% Tryptone, 0.5% yeast extract, 1.0% NaCl, 1.5% agar, Teknova, www.teknova.com, Cat. No. L1100) were inoculated with *Escherichia coli* (Strain S., Fisher Scientfic, www.fishersci.com, Cat. No. S20918). To verify the antibacterial properties of silver nanoparticles, a section of the agar surface was covered in silver nanopowder using the aerosol generator discussed in section 2.1. To test the silver-enhanced PVC material, 1.2×1.2 cm silver-enhanced PVC samples were placed coated side down onto the agar. Plates were incubated upside down in a lab oven at 37° C. for 24 hours and zones of inhibition were measured when possible.

2.8.2 Turbidity

To qualitatively establish whether or not samples exhibited antibacterial properties in aqueous solution, turbidity tests were conducted. Sterile Luria-Burtani (LB) broth (received from the University of Pennsylvania Department of Biology), was inoculated with *Escherichia coli*, and the resulting solution was placed in test tubes, 5 ml per tube. 1.2×1.2 cm PVC samples were immediately immersed in the solution in the tubes, one sample per test tube. Samples were incubated with loosened caps in a lab oven at 37° C. for 10 hrs and were observed for turbidity via visual examination at hours 1, 2, 3, 4, 5, 6, 8, and 10.

2.8.3 Growth Analysis

Antibacterial activity over time was assessed via growth analysis testing. The same initial procedure was used as for turbidity testing, as described elsewhere herein, but rather than perform visual observations, 200 µl of solution was removed from each test tube and plated on LB plates (1.0% Tryptone, 0.5% yeast extract, 1.0% NaCl, 1.5% agar (Teknova www.teknova.com, Cat. No. L1100) at hours 1, 2, 3, 4, 5, 6, 8, and 10. The plates were immediately refrigerated at 4° C. until 1 hour after all plates were collected. The plates were then incubated together in a lab oven at 37° C. and observed at hour 8. All samples were compared and a relative density scale was used, with 1 indicating lowest bacteria growth and 10 indicating highest bacteria growth. ImageJ was used to quantify the bacteria density for plates where a full lawn had not developed all 4 wt % Ag 2.25 wt % plates and that were not destroyed due to application of bad dye (hour 3, 4, 5, 6, and 8). The dye was intended to make the test results easier to analyze.

2.8.4 ASTM E2180

A FDA registered, independent microbiology laboratory (Accugen Laboratories, Inc. www.accugenlabs.com, Willowbrook, Ill.) was contracted to perform a certified ASTM-E2180 test (ASTM International www.astm.org.), which was the Standard Test Method for Determining the Activity of Incorporated Antimicrobial Agent(s) In Polymeric or Hydrophobic Materials. *Staphylococcus aureus* and *Escherichia coli* were used as challenge organisms, Dey Engley (DE) neutralizing broth was used as the neutralizer, contact time was 24 hours, and contact temperature was 35° C. Media and reagents used include soybean-casein digest agar, agar slurry, and sterile deionized water. A full protocol is available from ASTM International.

3. Results 3.1 Aerosol Treatment Method

The aerosol treatment method was explored in an attempt to develop a process that could be integrated directly into the current manufacturing process for PVC pipes. The method, as described in section 2.1, involved a process by which particles could be aerosolized directly onto the surface of freshly extruded pipes. Optical microscopy confirmed the adherence of silver particles to the surface of hot PVC, shown by FIG. 7, but also indicated significant agglomeration of the silver nanoparticles. While research efforts for the aerosol treatment method displayed promising results, the lack of access to an industrial twin-screw extruder and guidance in industrial manufacturing processes for PVC prevented further development of this method.

Figure 8:
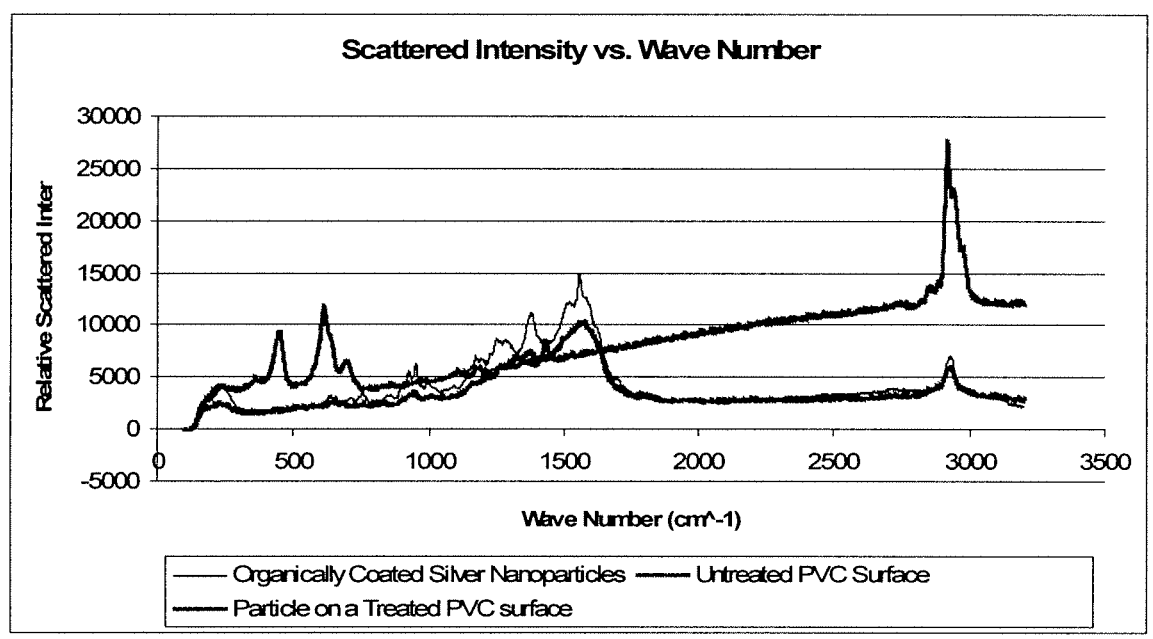
FIG. 8 illustrates Raman scattering associated with silver nanoparticles and the silver-enhanced and plain PVC samples.

3.2 Solvent Treatment Method 3.2.1 Surface And Particle Analysis 3.2.1.1 Raman Spectroscopy 50% argon-ion laser intensity was used for the preliminary scans of pure PVC and a strong Raman signal was recorded due to the highly reflective and white surface (FIG. 8). 1% light intensity was used for scans of silver-coated PVC samples (FIG. 8) in order to prevent burning associated with the high absorbance of the dark colored silver particles. This burning was later attributed to the burning off of the organic coating on the silver nanoparticles. While Raman spectroscopy would not pick up a signal from pure silver, the molecular bonds associated with the organic coating on the particles generated a Raman scattering signal (FIG. 8). The Raman signal from the silver-treated PVC substrate closely matched the signal from the organically coated silver nanoparticles, confirming the presence of the silver nanoparticles on the PVC surface. The peak in relative scattered intensity at ~3000 $cm^{-1}$ corresponded to a C—H bond and the peak at ~1580 $cm^{-1}$ corresponded to a C—C bond. Because the Raman signal from the silver-treated PVC substrate barely matched the signal from untreated PVC, it could be concluded that the silver particles were exposed on the substrate surface and not covered by PVC, thus allowing for the release of biocidal silver ions.

3.2.1.2 Optical Analysis

After confirming the identity of the particles on the surface of the PVC samples, optical microscopy was used to study the characteristics of the particulate dispersions (average particle size and area fraction of surface coverage) in order to optimize the embedding process. Average particle size and embedded area fraction values were significantly influenced by the concentration of PVC powder and silver in the THF solution. PVC powder was added to the solution in order to stabilize the silver suspension (i.e. retard agglomeration over time) and encourage smaller silver particles by increasing steric repulsion.

Figure 9:
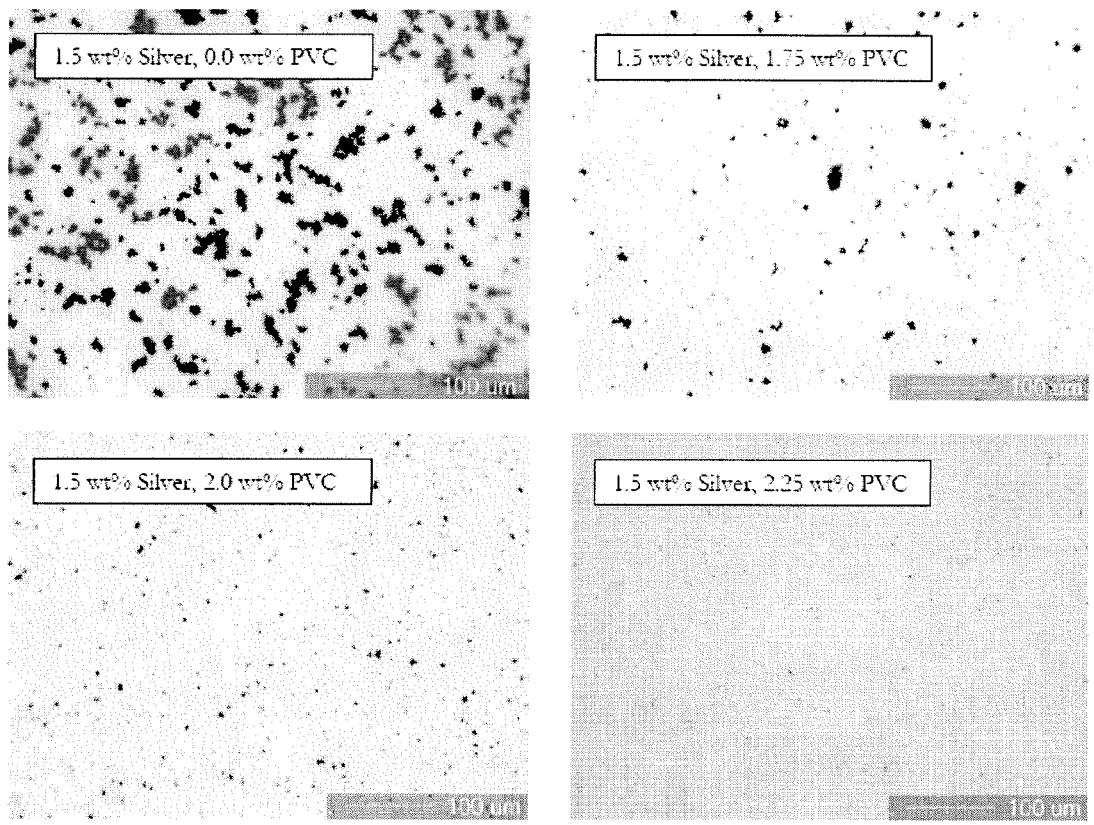
FIG. 9 illustrates optical micrographs of PVC samples treated with silver containing tetrahydrofuran (THF) solutions containing varying concentrations of PVC but constant silver concentration (1.5 wt %) at 20× magnification.

Silver particles in silver-THF solutions prepared without the addition of PVC visibly settled out faster than the silver particles in PVC-stabilized solutions, prepared with identical silver concentrations. Silver nanoparticles also agglomerated to a greater extent in silver-THF solutions not stabilized with PVC. This greater agglomeration was evident in the fact that average size of the silver particles on PVC substrates treated with unstabilized silver-THF solutions was larger (radius ~6.3 μm for solution with 1.5 wt % silver and 0 wt % PVC) than the size of particles on substrates treated with stabilized solutions (radius 466.6 nm for solution with 1.5 wt % silver and 2.25 wt % PVC) (FIG. 9). As shown in FIG. 9, the average size of the silver particles on the PVC substrates also decreased with increasing PVC concentration, thus indicating that PVC retarded agglomeration and allowed for smaller particle size. However, such a trend was not always achieved for increasing PVC concentrations owing to various sources of error and possibly complex relations between the concentration of silver and PVC added to the silver-THF solutions.

Figure 10:
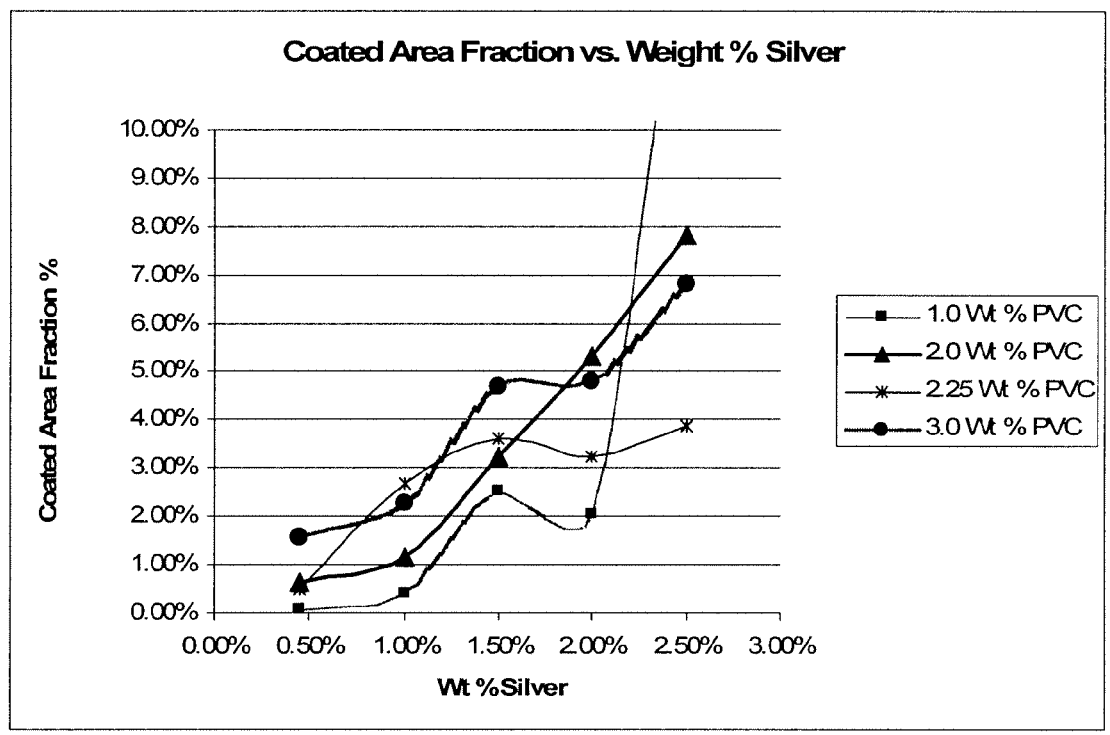
FIG. 10 illustrates the coated area fraction with increasing silver concentration for various constant PVC concentrations.

Area fractions of the PVC samples embedded with silver strongly depended on the concentration of silver in the silver-THF solutions. For constant concentrations of PVC, the area fraction of surface coverage generally increased with increasing silver concentration (FIG. 10). Area fraction of surface coverage data corresponding to all PVC concentrations exhibited a dip on increasing the silver concentration from 1.5 wt % to 2.0 wt % (FIG. 10). Furthermore, the magnitude of this dip decreased with increasing PVC concentration. A possible explanation was that 1.5-2.0 wt % silver represented some sort of agglomeration threshold and that higher silver concentrations resulted in agglomeration, which in turn reduced the area fraction of surface coverage. Because higher PVC concentrations prevented agglomeration to a greater degree, the decrease in area fraction of surface coverage became less significant with increasing PVC concentration. However, the overall data set was noisy due to limitations in the image analysis software and several sources of error discussed later.

As shown in FIG. 10, area fractions of surface coverage corresponding to silver-THF solutions stabilized with higher concentrations of PVC powder were in general higher than the area fractions of surface coverage corresponding to solutions with lower PVC concentrations. Without being bound to a single theory of operation, it is believed that this supports the theory that PVC powder helped stabilize the silver suspension and prevented agglomeration, thus leading to smaller and more finely dispersed silver particles on PVC substrates.

Figure 11:
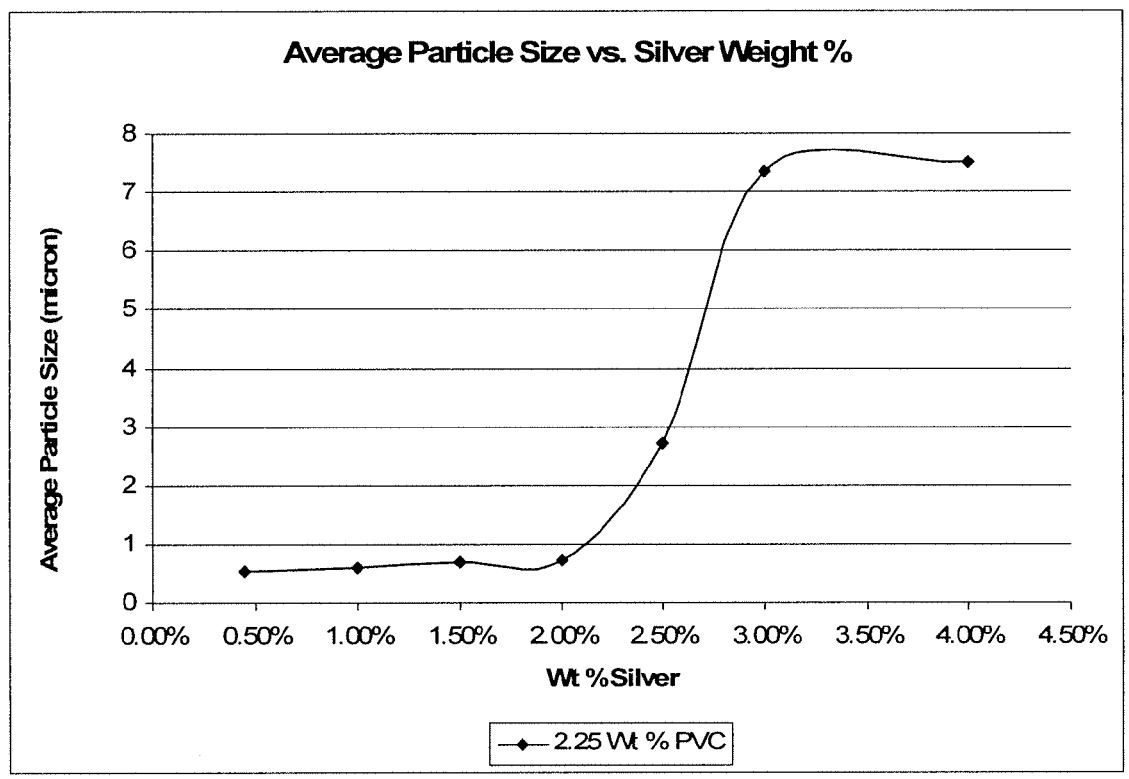
FIG. 11 illustrates an increasing trend in average particle size with increasing silver concentration at constant PVC concentration.

Average particle size also depended on silver concentration. FIG. 11 demonstrates the following trend in average particle size: for low values of silver concentration, average particle size increased slightly with increasing silver concentration; at a critical agglomeration threshold (1.5-2.0 wt % silver), average particle size increased rapidly; for high values of silver concentration, average particle size stabilized. Without being bound to any single theory of operation, it is believed that a given amount of stabilizer, 2.25 wt % PVC as in FIG. 11, can prevent agglomeration only up to certain silver concentrations, after which the stabilization effect—steric repulsion—was minimal and particles agglomerated substantially. Depletion attraction and bridging effects may also explain the agglomeration.

Average particle size and area fraction of surface coverage data were subject to severe limitation in the image analysis software and several sources of error. While the Particle Analysis tool in ImageJ was very accurate, the process by which the optical images were converted to binary black and white images for the purpose of analysis was subject to considerable human error. A substantial amount of human judgment was used to adjust the gray-scale color used as a threshold to define the boundary of the silver particles such that the software picked up all the smaller particles and large agglomerates, while eliminating unwanted reflections and light variations. While the area-fraction data was not affected significantly by such judgment calls, the average particle size data was very strongly dependant on the threshold levels. Therefore the average particle size data could reflect significant inaccuracy. Thus, trends in average particle size were easier to interpret visually through the optical micrographs (FIG. 9).

3.2.2 Durability Analysis

SEM images of a silver particle on the surface of PVC cut in half using a FIB (FIG. 12) show that the particles are embedded into the PVC substrate. The small dots surrounding the silver particle in the figure represent the palladium gold coating, which was visible due to the burning of the underlying PVC substrate by the ion and electron beams. The features present in the wall of the trench cut by the FIB were unknown, but were also observed in the cross-section of an un-coated PVC sample (FIG. 12). Without being bound to any one theory, it is believed that these features are stabilizers, such as aluminum, added to industrial PVC to aid processing. Embedding the silver particles into the PVC was the desired result of using THF as a dispersion medium since it was known to dissolve PVC in addition to most other plastics (ImageJ, http://rsb.info.nih.gov/ij/).

Figure 13:
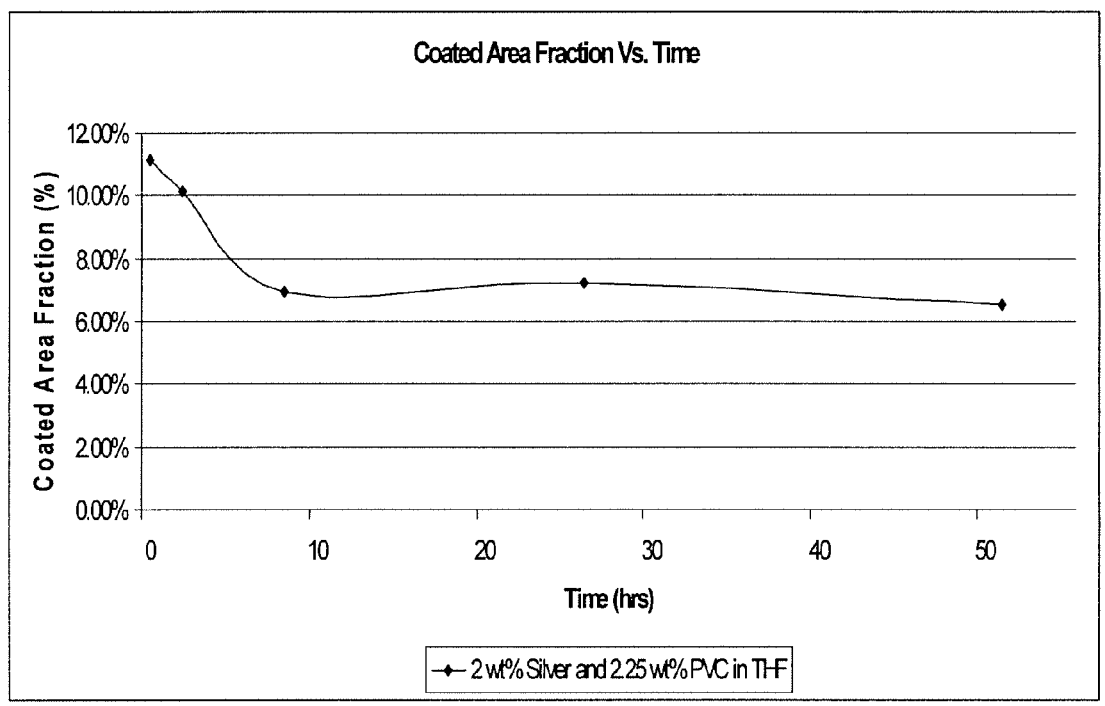
FIG. 13 illustrates the area fraction of silver coverage over time for PVC samples enhanced with a 2 wt % silver and 2.25 wt % PVC in THF solution subject to a water flow rate of 3.9 gal/min·in$^2$.

Embedding the silver particles allowed for a durable silver surface treatment that would resist erosion with continuous water flow. The preliminary durability test showed that the silver-coated area fraction of the PVC samples decreased over the first few hours of exposure to water flow but stabilized for up to 40 hours past this point, as shown in FIG. 13. The initial decrease could have been due to the erosion of the silver particles that were loosely embedded or not embedded into the PVC surface. Durability tests for longer timescales, for example time periods closer to the useful life of PVC pipe, remain to be conducted.

Figure 14:
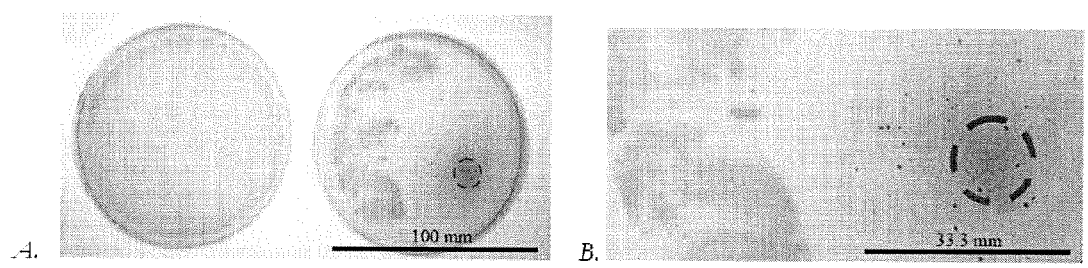
FIG. 14 illustrates (A) 100 mm Liria-Bertani (LB broth) plates 24 hours after inoculation with *E. coli*. Control (left plate) and with aerosolized Ag nanoparticles (right plate), with red dotted circle showing target of the air stream, (B) expanded view of bacteria growth boundary regions in FIG. 14A, with a dotted circle showing the target of the air stream.

3.2.3 Antibacterial Analysis 3.2.3.1 Kirby-Bauer Test Results For Antimicrobial Properties of Silver Nanoparticles For experimental rigor, the antibacterial properties of the silver nanoparticles used for surface treatment in the current research were qualitatively verified. Modified Kirby-Bauer tests showed that nanoparticle powder distributed across the surface of agar plates via aerosolization inhibited the growth of *Escherichia coli* (FIG. 14). Due to the distributed nature of the deposition technique, measuring zones of inhibition was not possible. However, it is clear that the lawn formation that occurred in control samples without any silver particles (FIG. 14A, left plate) was inhibited by the presence of silver nanopowder on the surface of the agar (FIG. 14A, right plate). Increasing the amount of silver nanopowder spread across the surface led to an increased antibacterial inhibition, to the point where no bacteria growth was observed.

3.2.3.2 Kirby-Bauer Test Results For Antimicrobial Properties of Silver Nanoparticle Enhanced Polyvinyl Chloride The Kirby-Bauer test is routinely used to observe the activity of antibiotics. The test involves the placement of paper discs soaked in the target antibiotic on the agar surface of bacteria growth plates. The antibiotic diffuses into the agar, and inhibition of bacteria growth is observed around the discs. The diameters of these zones of inhibition are then measured and compared for determining relative antibiotic effectiveness. In the current study, silver-enhanced PVC samples were placed treated side down on inoculated agar plates; thus, diffusion of silver ions from the coating through the agar was the only theoretical mechanism by which zones of inhibition could form.

Figure 15:
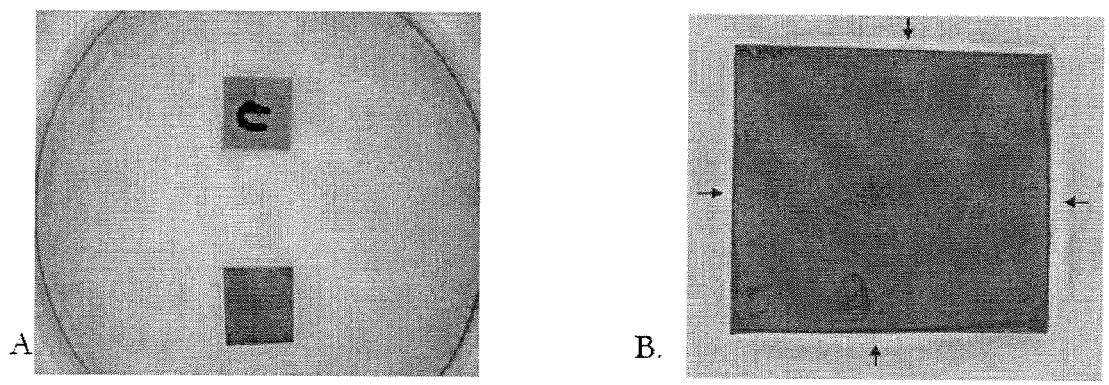
FIG. 15 illustrates (A) an untreated control sample (top, labeled with a "C") and a sample treated with 2 wt % Ag, 2.25 wt % PVC in THF (bottom) as viewed from underside of agar 24 hours following inoculation with *E. coli*, and (B) an expanded view of the treated sample from (A), with arrows pointing to zone of inhibition maxima (−0.88 mm)

FIG. 15A shows an uncoated control sample at the top of the figure, and a 2 wt % Ag 2.25 wt % PVC treated sample at the bottom of the figure, as viewed from the underside of a petri dish 24 hours after inoculation with *E. coli*.

Results show the formation of a small zone of inhibition, about 0.88 mm wide at the maxima of the sides of the samples, FIG. 15B, in test samples. The region of no growth was largest towards the center of the sides of the sample, consistent with the pattern expected if diffusion of ions occurred. Discoloration of the agar was not observed, which suggested that the zones of inhibition were not formed as a result of detachment of embedded silver particles. Thus, given the shape and color of the zones of inhibition, ion diffusion is the suspected mechanism by which zones of inhibition formed.

3.2.3.3 Turbidity Test Results

Figure 16:
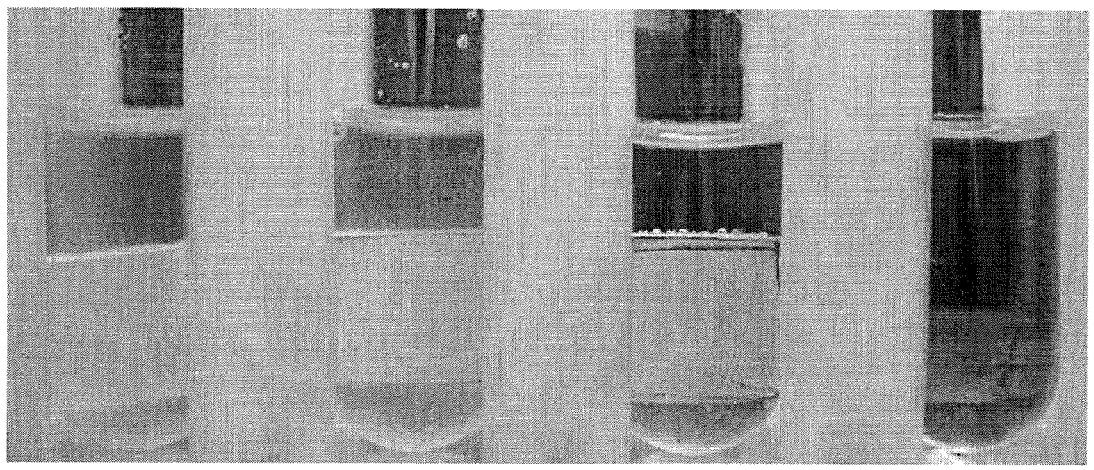
FIG. 16 illustrates an untreated control sample (left-most sample), a sample treated with 2 wt % Ag, 2.25 wt % PVC, THF solution (second from left), a sample treated with 4 wt % Ag, 2.25 wt % PVC, THF solution (third from left), and sterile LB broth (right) after 10 hours. Each test tube containing a sample contained LB broth inoculated with equivalent concentration of *E. coli*, and the decreased turbidity of the broth containing more heavily treated samples indicates inhibition of *E. coli* bacterial growth.
Figure 17:
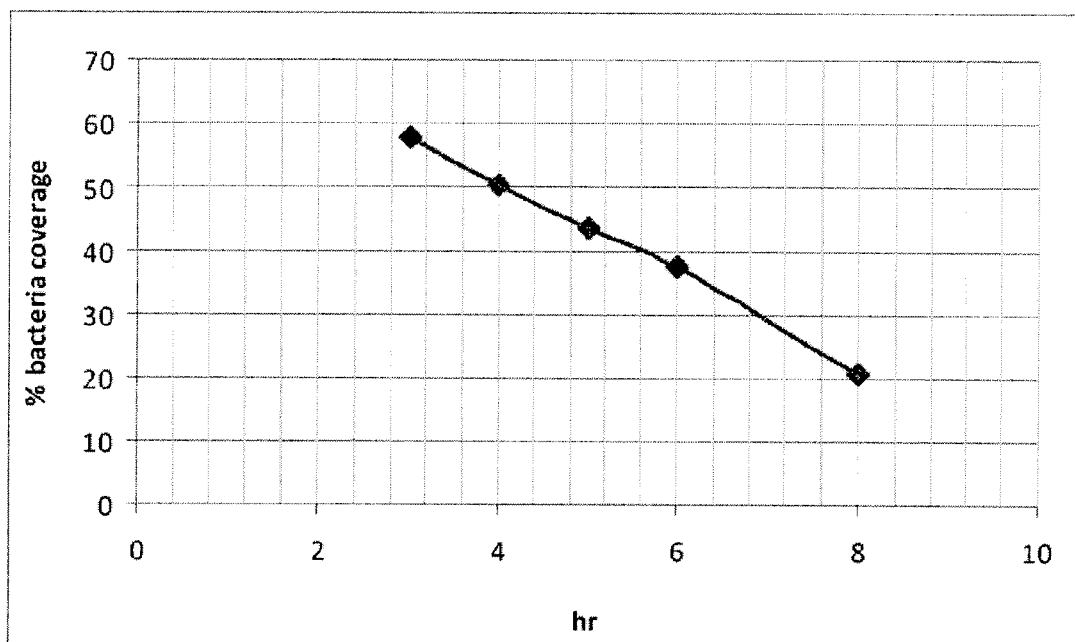
FIG. 17 illustrates percentage bacteria coverage of LB agar plates versus time for *E. coli-inolculated* LB broth in contact with a 4.0 wt % Ag and 2.0 wt % PVC sample and then spread plated.
Figure 18:
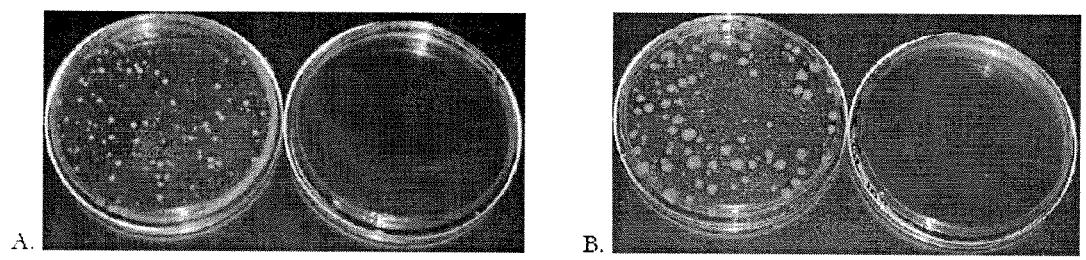
FIG. 18 illustrates (A) growth of *E. coli* on untreated control sample after 24 hours (left), and reduction of growth of *E. coli* on a sample treated with 4 wt % Ag, 2.25 wt % PVC, THF solution (right), and (B) growth of *S. aureus* on untreated control sample after 24 hours (left), and reduction of growth of *S. aureus* on a sample treated with 4 wt % Ag, 2.25 wt % PVC, THF solution (right)

Turbidity is directly related to the number of bacteria cells in a given solution. By hour 4, the Control and 2 wt % Ag 2.25 wt % PVC samples exhibited high turbidity relative to the 4 wt % Ag 2.25 wt % PVC samples and to the sterile LB broth. The 4 wt % Ag 2.25 wt % PVC samples exhibited similar translucence as the sterile LB broth. The samples were observed at hours 5, 6, 8, and 10 (FIG. 16), but no visible change in turbidity was observed for any samples. From these results, it appears that the treated PVC samples exhibit antibacterial activity, correlated with weight percent silver.

3.2.3.4 ASTM E2180 Results

The ASTM E2180 test is a standardized test, "designed to evaluate (quantitatively) the antimicrobial effectiveness of agents incorporated or bound into or onto mainly flat (two dimensional) hydrophobic or polymeric surfaces . . . . This method can confirm the presence of antimicrobial activity in plastics or hydrophobic surfaces and allows determination of quantitative differences in antimicrobial activity between untreated plastics or polymers and those with bound or incorporated low water-soluble antimicrobial agents" [1.0% Tryptone, 0.5% yeast extract, 1.0% NaCl, 1.5% agar. Teknova, www.teknova.com, Cat. No. L1100]. An agar slurry was used to form a pseudo-biofilm on the surface, reducing surface tension and providing more contact between the inoculum and the test surface. The ASTM E2180 results demonstrate a 100% reduction in the activity of all microorganisms within the first 24 hours of exposure to the 4 wt % Ag 2.25 wt % PVC samples. Both Gram-positive (*S. aureus*) and Gram-negative (*E. coli*) bacteria were affected. This conclusive and quantitative data is corroborated by the qualitative data collected via the modified Kirby-Bauer, Turbidity, and Growth Analysis tests. Percent reduction in growth was obtained as follows:

$$\% \text{ Reduction for } S.\ aureus = \frac{(a-b) \times 100}{a} = \frac{(1.51 \times 10^5 - 0) \times 100}{1.51 \times 10^5} = 100\%$$

$$\% \text{ Reduction for } E.\ coli = \frac{(a-b) \times 100}{a} = \frac{(5.13 \times 10^5 - 0) \times 100}{5.13 \times 10^5} = 100\%$$

where, a=the antilog of the geometric mean of the number of organisms recovered from the control samples after 24 hours and b=the antilog of the geometric mean of the number of organisms recovered from the treated samples after 24 hours.

Results show presence of antimicrobial activity (100% reduction for *S. aureus*, 100% reduction for *E. coli*).

4. Summary of PVC-Silver Results

Industrial-grade flat PVC sheets were embedded with silver particles and the antibacterial properties of the resulting surface were confirmed. Silver nanopowder was suspended in THF and PVC solution and spin-coated onto flat PVC substrates at concentrations of 0.45 wt % to 4.0 wt %. PVC powder was used as a stabilizer at concentrations from 0.0 wt % to 3.0 wt %. Raman spectroscopy confirmed the identity of the embedded particles as the organically coated silver nanoparticles. Optical microscopy and ImageJ software were used to measure area fraction of embedded surface coverage and average particle size for all samples. Embedded surface area fractions ranged from 0.1%-20% and particle-agglomerate radii from 73 nm to 400 nm Desired area fraction of embedded surface coverage and particle size dispersion were controlled by varying the concentration of silver and PVC powder in the solution. Dissolving PVC powder in the silver solution helped stabilize the suspension, retarding agglomeration.

Increasing PVC concentration, in general, led to smaller particle size and greater area fraction of embedded surface coverage. Increasing silver concentrations, at constant PVC concentrations, resulted in higher area fractions of embedded surface coverage and larger average particle size. Durability testing indicated that after an initial drop in area fraction, the embedded particles withstood continuous water-flow and remained securely embedded in the surface. SEM imaging confirmed that the silver particles were embedded into the PVC substrate.

Antibacterial tests (Kirby-Bauer, Turbidity, and ASTM E2180) were conducted using Gram-positive (*Staphylococcus aureus*) and Gram-negative (*Escherichia coli*) bacteria. Test results demonstrated the antibacterial properties of silver treated samples. In particular, ASTM E2180 showed that test samples coated with 4.0 wt % silver reduced *S. aureus* and *E. coli* activity by 100% within 24 hours. The treatment process developed in this research can be adapted for a variety of particles, substrates, and solvents. Thus, potential applications range from PVC pipes that purify water to materials that neutralize bio/chemical threats.

What is claimed:

1. A method of embedding particles in a substrate, comprising:
applying to at least a portion of a substrate a fluid and a population of particles comprising metallic nanowires, such that the substrate is softened to at least a degree that a plurality of individual particles is at least partially embedded in the softened portion of the substrate; and
hardening the softened portion of the substrate so as to securely embed the plurality of particles in the substrate, wherein the plurality of particles securely embedded in the substrate forms a conductive pathway by touching or proximity of the particles to one another.

| | Microorganisms recovered in 4 wt % Ag, 2.25 wt % PVC sample after 24 hours (cfu/ml) | | | | Microorganisms recovered in Control sample after 24 hours (cfu/ml) | | | |
|---|---|---|---|---|---|---|---|---|
| | Trial 1 | Trial 2 | Trial 3 | Geom. Mean | Trial 1 | Trial 2 | Trial 3 | Geom. Mean |
| S. aureus | <10 | <10 | <10 | 0 | $1.38 \times 10^5$ | $2.25 \times 10^5$ | $1.15 \times 10^5$ | 5.18 |
| E. coli | <10 | <10 | <10 | 0 | $4.6 \times 10^5$ | $5.7 \times 10^5$ | $5.1 \times 10^5$ | 5.71 |

2. The method of claim 1, wherein applying the fluid and the population of particles comprises softening the substrate using the fluid.

3. The method of claim 1, wherein the fluid comprises a solvent that softens the substrate, and wherein applying the fluid and the population of particles comprises disposing the population of particles in the fluid, and applying the fluid and the population of particles over the substrate.

4. The method of claim 1, wherein the fluid further comprises a salt, a surfactant, a stabilizer to inhibit inter-particle agglomeration, or any combination thereof.

5. The method of claim 1, wherein the population of particles is disposed in the fluid at a concentration up to 4 wt %.

6. The method of claim 1, wherein applying the fluid and the population of particles further comprises application of a magnetic field or an electric field to control a degree of embedding of at least one particle.

7. The method of claim 1, wherein the population of particles comprises silver.

8. The method of claim 1, wherein the substrate comprises a polymer.

9. The method of claim 1, wherein at least one of the plurality of particles is fully embedded below a surface of the substrate.

10. The method of claim 1, wherein the plurality of particles securely embedded within the substrate forms a conductive pathway by touching of the particles to one another.

11. A method of embedding particles in a substrate, comprising:
    providing a substrate;
    providing a population of particles selected from at least one of nanowires, nanorods, and nanotubes; and
    using a fluid, softening the substrate such that one or more of the population of particles is at least partially embedded in the substrate,
    wherein at least one individual particle of the population of particles is fully embedded below a surface of the substrate,
    wherein multiple ones of the population of particles are embedded in the substrate to form a conductive pathway by touching or proximity of the particles to one another.

12. The method of claim 11, wherein the population of particles is disposed in the fluid.

13. The method of claim 11, wherein softening the substrate comprises applying the fluid to the substrate.

14. The method of claim 11, wherein the substrate comprises a polymer, and the fluid comprises a solvent for the polymer.

15. The method of claim 11, wherein the population of particles comprises metallic nanowires.

16. The method of claim 11, further comprising removing at least a portion of the fluid to harden the substrate.

* * * * *